(12) United States Patent
Betzi et al.

(10) Patent No.: US 11,180,510 B2
(45) Date of Patent: Nov. 23, 2021

(54) XANTHINE DERIVATIVES AND USES THEREOF AS INHIBITORS OF BROMODOMAINS OF BET PROTEINS

(71) Applicants: Centre national de la recherche scientifique, Paris (FR); Université d'Aix-Marseille, Marseilles (FR); INSTITUT NATIONAL DE LA SANTE ET DE LA RECHERCHE MEDICALE (INSERM), Paris (FR)

(72) Inventors: Stéphane Betzi, Marseilles (FR); Sébastien Combes, Fuveau (FR); Yves Collette, Marseilles (FR); Laurent Hoffer, Marseilles (FR); Xavier Morelli, Marseilles (FR); Brigit Raux, Grenade (FR); Philippe Roche, Marseilles (FR); Iuliia Voitovich, Marseilles (FR)

(73) Assignees: CENTRE NATIONAL DE LA RECHERCHE SCIENTIFIQUE, Paris (FR); UNIVERSITÉ D'AIX-MARSEILLE, Marseilles (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 16/762,069

(22) PCT Filed: Nov. 6, 2018

(86) PCT No.: PCT/EP2018/080345
§ 371 (c)(1),
(2) Date: May 6, 2020

(87) PCT Pub. No.: WO2019/086712
PCT Pub. Date: May 9, 2019

(65) Prior Publication Data
US 2020/0377522 A1      Dec. 3, 2020

(30) Foreign Application Priority Data
Nov. 6, 2017     (EP) .................................. EP17306532

(51) Int. Cl.
| | |
|---|---|
| *A61K 31/522* | (2006.01) |
| *C07D 519/00* | (2006.01) |
| *C07D 333/20* | (2006.01) |
| *C07D 409/12* | (2006.01) |
| *C07D 473/04* | (2006.01) |

(52) U.S. Cl.
CPC ......... *C07D 519/00* (2013.01); *C07D 333/20* (2013.01); *C07D 409/12* (2013.01); *C07D 473/04* (2013.01)

(58) Field of Classification Search
None
See application file for complete search history.

(56) References Cited

U.S. PATENT DOCUMENTS

| | | |
|---|---|---|
| 2015/0307493 A1 | 10/2015 | Combs et al. |
| 2017/0158689 A1 | 6/2017 | Combs et al. |
| 2018/0312506 A1 | 11/2018 | Combs et al. |

FOREIGN PATENT DOCUMENTS

| | | |
|---|---|---|
| WO | WO-2015164480 | 10/2015 |
| WO | WO-2017114843 | 7/2017 |

OTHER PUBLICATIONS

International Search Report dated Dec. 7, 2018 in International Application No. PCT/EP2018/080345.
Partial European Search Report dated Feb. 7, 2018 in European Application No. 17 30 6532.

*Primary Examiner* — Samantha L Shterengarts
(74) *Attorney, Agent, or Firm* — B. Aaron Schulman., Esq.; Stites & Harbison, PLLC

(57) ABSTRACT

The present invention relates to a compound having the following formula (I): (I) wherein: —R is a $(C_1$-$C_6)$alkyl group; —R" is preferably H; —Ar is a $(C_5$-$C_{12})$arylene radical; —$X_1$ is —C(=O)— or —$SO_2$—; and —R' is chosen from the group consisting of possibly substituted $(C_1$-$C_6)$ alkyl, heteroaryl, $(C_5$-$C_{12})$aryl, and (hetero)cycloalkyl groups, or a pharmaceutically acceptable salt and/or tautomeric form thereof, or its racemates, diastereomers or enantiomers.

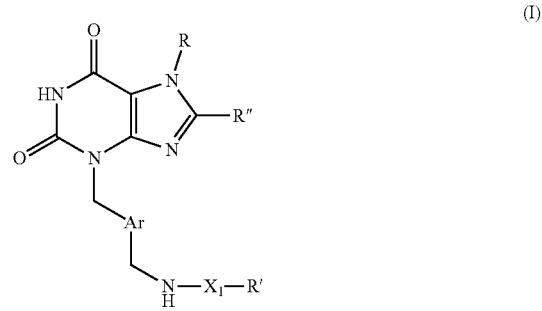

11 Claims, 4 Drawing Sheets

XANTHINE DERIVATIVES AND USES THEREOF AS INHIBITORS OF BROMODOMAINS OF BET PROTEINS

The present invention concerns xanthine derivatives, their preparation process as well as their uses as inhibitors of bromodomains of BET proteins.

Bromodomains (BRD) are protein domains called protein interaction modules that preferentially bind ε-N-acetylated lysine residues through structurally well-defined pockets. BRDs are found in 8 protein families which include a total of 46 nuclear or cytoplasmic proteins in human with diverse structures and functions, including chromatin-modifying enzymes, helicases, chromatin remodelers, transcriptional co-activators and mediators, and the bromodomain and extra-terminal domain (BET) family of proteins. BET proteins (BRD2, BRD3, BRD4, and the testis-specific BRDT) have a conserved modular architecture including two N-terminal tandem BRDs (BD1 and BD2). The BETs play a central role in chromatin biology by acting as tissue-specific recruitment platforms that tether complexes to acetylated histones and chromatin, facilitating the assembly of the transcriptional machinery and controlling genes expression in inflammation, viral infection and cancer biology. For example, BRD2 is specifically recruited to acetylated histones H3 and H4 and this interaction is linked to active transcription and mitosis. BRD2 and BRD3 are required for permissive RNA polymerase II transcription through acetylated nucleosomes and it has been suggested that BRD4 binds acetylated histones using primarily its first bromodomain (BD1). The BD2 domain also recognizes and interacts with the acetylated region of cyclin T1 which forms a complex with the positive transcription elongation factor b and is crucial for the sustained presence of Pol II in active genes and for transcription initiation and elongation, thereby regulating the expression of cell proliferation supporting genes, including c-Myc and its target genes.

BET proteins are often deregulated in diseases, their transcription-regulating activity being altered and thus affecting numerous growth-promoting genes and cytokines. BET proteins are known to be deregulated in cancer and the recent disclosure of pan-BET inhibitors (multi-targeted BET inhibitors) that attenuate BRD function has allowed the validation of these drug targets, shedding light on their roles in such diseases. Interestingly, BRD4 occupies "super-enhancers" and its inhibition leads to significant reduction of the transcript levels of only a few hundred genes, in a cell-, disease- and context-specific manner. Alongside, preclinical targeting of BETs has had initial successes, particularly in oncology. For example, in a phase I acute leukemia study, (6S)-4-(4-chlorophenyl)-N-(4-hydroxyphenyl)-2,3,9-trimethyl-6H-thieno[3,2-f][1,2,4]triazolo[4,3-a][1,4]diazepine-6-acetamide (OTX015), a thienodiazepine, induced remissions, including complete remission in two patients with refractory disease. 2-[4-(2-hydroxyethoxy)-3,5-dimethylphenyl]-5,7-dimethoxy-4(3H)-quinazolinone (RVX-208), a quinazolone derivative of resveratrol that binds preferentially to the BD2 domain of BRD2 and BRD3 has already been tested in hundreds of patients in phase II clinical trials for the treatment of atherosclerosis, providing proof-of-concept that selective inhibition within the BET family is feasible.

A permanent wavering in drug discovery is related to the development of pan- or selective (single targeted-) inhibitors. Indeed, pan-BET inhibition might remain an issue regarding the impact on numerous transcriptional pathways and the individual tissue specific functions of BET members. Furthermore, there are potential drawbacks concerning the use of pan-BET inhibitors with strong risks of 'off-target' effects and/or appearance of resistances.

Therefore, the selective targeting of individual BET and the discrimination between BD1 and BD2 present an opportunity to achieve more selective transcriptional effects.

The aim of the present invention is thus to provide new compounds being efficient inhibitors of bromodomains.

Another aim of the present invention is to provide new selective inhibitors, having also an improved inhibition activity, preferably in the nanomolar range.

Another aim of the present invention is to provide selective inhibitors of a single bromodomain of a given BET protein.

Another aim of the present invention is to provide compounds inhibiting selectively the BD1 domain of BRD3 and BRD4 in the nanomolar range, but which do not inhibit (or only inhibit in the micromolar range) the BD2 domain.

Thus, the present invention relates to a compound having the following formula (I):

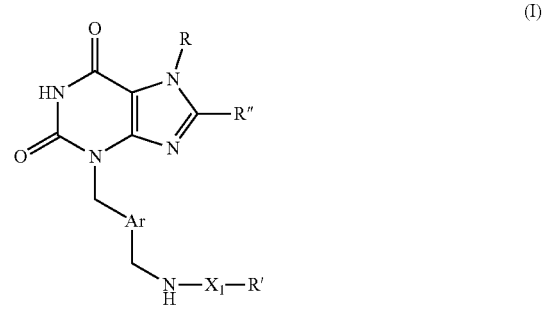

wherein:

R is a $(C_1-C_6)$alkyl group;

R" is H or a group having the following formula (A):

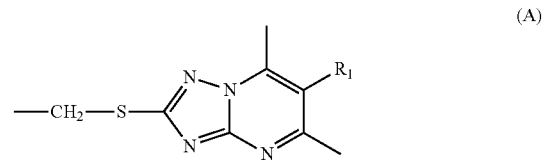

wherein $R_1$ is H or a $(C_1-C_6)$alkyl group; preferably H or a butyl group;

Ar is a $(C_5-C_{12})$arylene radical;

$X_1$ is —C(=O)— or —SO$_2$—; and

R' is chosen from the group consisting of:
- $(C_1-C_6)$alkyl groups, possibly substituted with one or several substituents selected from:
  - $(C_5-C_{12})$aryl, optionally substituted by a $(C_1-C_6)$ alkyl group,
  - S—OR$_a$, R$_a$ being selected from: H, and $(C_1-C_6)$ alkyl, R$_a$ being preferably H,
  - —NH$_2$,
  - —NH—C(=O)—O—$(C_1-C_6)$alkyl, and
  - (hetero)cycloalkyl;
- heteroaryl groups, possibly substituted with one or several substituents selected from:
  - $(C_1-C_6)$alkyl,
  - $(C_5-C_{12})$aryl, and heteroaryl groups, optionally substituted by a $(C_1$-$C_6)$alkyl group;

$(C_5$-$C_{12})$aryl groups, possibly fused with one heterocycloalkyl or heteroaryl group, optionally substituted with one or several substituents selected from: $(C_1$-$C_6)$alkyl, and $COR_2$, $R_2$ being a $(C_1$-$C_6)$alkyl group;

said aryl group being possibly substituted with one or several substituents selected from:

$(C_1$-$C_6)$alkyl, $(C_5$-$C_{12})$aryl, heteroaryl, optionally substituted by a $(C_1$-$C_6)$alkyl group, —$CH_2$-heteroaryl, heterocycloalkyl, optionally fused with a phenyl group,

—$NO_2$, $OR_a$, $R_a$ being selected from: H, $(C_1$-$C_6)$alkyl, $(C_5$-$C_{12})$aryl, and —$CH_2$—$(C_5$-$C_{12})$aryl, —$NR_bR_c$, $R_b$ and $R_c$, being, independently of one another, H or $(C_1$-$C_6)$alkyl, and $R_b$ and $R_c$, being preferably H, and —$NHC(=O)R_d$, $R_d$ being a $(C_1$-$C_6)$alkyl group;

(hetero)cycloalkyl groups, comprising 5 or 6 atoms and optionally one heteroatom, possibly substituted with one or several substituents selected from:

$(C_1$-$C_6)$alkyl,

—$C(=O)R_d$, $R_d$ being a $(C_1$-$C_6)$alkyl group,

—$OR_d$, $R_d$ being a $(C_1$-$C_6)$alkyl group,

—$CH_2$—$OR_d$, $R_d$ being a $(C_1$-$C_6)$alkyl group, $(C_5$-$C_{12})$aryl,

—$C(=O)OR_d$, $R_d$ being a $(C_1$-$C_6)$alkyl group,

—$CH_2$—$NHC(=O)OR_d$, $R_d$ being a $(C_1$-$C_6)$alkyl group, and

—$NHC(=O)OR_d$, $R_d$ being a $(C_1$-$C_6)$alkyl group;

or a pharmaceutically acceptable salt and/or tautomeric form thereof, or its racemates, diastereomers or enantiomers.

In formula (I), R' may also be chosen from $(C_5$-$C_{12})$aryl groups, possibly fused with one heterocycloalkyl or heteroaryl group, optionally substituted with one or several substituents selected from: $(C_1$-$C_6)$alkyl, and $COR_2$, $R_2$ being as defined above, said aryl group being possibly substituted with one or several substituents selected from:

$(C_1$-$C_6)$alkyl, $(C_5$-$C_{12})$aryl, heteroaryl, optionally substituted by a $(C_1$-$C_6)$alkyl group, halogen, —$CH_2$-heteroaryl, heterocycloalkyl, optionally fused with a phenyl group,

—$NO_2$,

—$OR_a$, $R_a$ being selected from:

H, $(C_1$-$C_6)$alkyl, $(C_5$-$C_{12})$aryl, optionally substituted with a substituent chosen from the halo$(C_1$-$C_6)$alkyl groups, in particular $CF_3$, cycloalkyl, heteroaryl, optionally substituted with a substituent chosen from the $(C_1$-$C_6)$alkyl groups, such as methyl, heterocycloalkyl, optionally substituted with a substituent, in particular chosen from the $(C_1$-$C_6)$alkyl groups, such as methyl, and the $(C_1$-$C_6)$alkylene-$(C_2$-$C_6)$alkynyl groups, and —$CH_2$—$(C_5$-$C_{12})$aryl, —$C(=O)$—$R_e$, $R_e$ being a heterocycloalkyl, —$NR_bR_c$, $R_b$ and $R_c$, being, independently of one another, H or $(C_1$-$C_6)$alkyl, and $R_b$ and $R_c$, being preferably H, and —$NHC(=O)R_d$, $R_d$ being a $(C_1$-$C_6)$alkyl group.

The compounds of formula (I) are BET protein inhibitors, and in particular, selective inhibitors of a given bromodomain.

The term "BET protein" or "BET family member" in the present invention refers to a BET protein chosen from the group consisting of: BRD2, BRD3, BRD4 and BRDT.

The term "bromodomain" in the present invention refers to the bromodomain BD1 or BD2 of a BET protein.

The term "BET protein inhibitor" in the present invention refers to a compound that binds to the target BET protein, in particular binds to the target bromodomain (BD1 or BD2) of a BET protein with measurable affinity, and decreases its activity. Typically, according to the invention, an inhibitor binds to a BET protein and in particular to a bromodomain of a BET protein, thus decreasing the activity of the BET protein.

The compounds of formula (I) can comprise one or more asymmetric carbon atoms. They can therefore exist in the form of enantiomers or of diastereoisomers. These enantiomers and diastereoisomers, and also mixtures thereof, including racemic mixtures, form part of the invention.

The compounds of formula (I) can exist in the form of bases or of addition salts with acids. Such addition salts form part of the invention.

The compounds of formula (I) can exist in the form of pharmaceutically acceptable salts.

These salts can be prepared with pharmaceutically acceptable acids, but the salts of other acids that are of use, for example, for purifying or isolating the compounds of formula (I) also form part of the invention.

The term "pharmaceutically acceptable salt" in the present invention means that all pharmaceutically acceptable salts of the inhibitor according to the invention are included within the scope of the invention, in particular the salts of weak acids and of weak bases. Examples of salts include hydrochloride, hydrobromide, potassium acetate, sodium acetate, calcium acetate, ammonium chloride, potassium carbonate, sodium carbonate, calcium carbonate, potassium bicarbonate, sodium bicarbonate, and calcium bicarbonate.

The term "tautomeric forms" in the present invention refers to tautomers of nucleobases, i.e: constitutional isomers of nucleobases.

In the context of the present invention:

the expression "$C_t$-$C_z$ where t and z can take the values from 1 to 6" means a carbon-based chain which can have from t to z carbon atoms, for example $C_1$-$C_3$ means a carbon-based chain which can have from 1 to 3 carbon atoms;

the term "a halogen atom" means: a fluorine, a chlorine, a bromine or an iodine;

the term "an alkyl group" means: a linear or branched, saturated, hydrocarbon-based aliphatic group comprising, unless otherwise mentioned, from 1 to 6 carbon atoms. By way of examples, mention may be made of methyl, ethyl, n-propyl, isopropyl, butyl, isobutyl, tert-butyl or pentyl groups;

the term "a haloalkyl group" means: an alkyl group as defined above, in which one or more of the hydrogen atoms is (are) replaced with a halogen atom. By way of example, mention may be made of fluoroalkyls, in particular $CF_3$ or $CHF_2$;

the term "a cycloalkyl group" means: a cyclic carbon-based group comprising, unless otherwise mentioned, from 3 to 6 carbon atoms. By way of examples, mention may be made of cyclopropyl, cyclobutyl, cyclopentyl, cyclohexyl, etc. groups;

the term "aryl group" means: a cyclic (mono- or polycyclic) aromatic group comprising between 5 and 12 carbon atoms, unless otherwise specified. By way of examples of aryl groups, mention may be made of phenyl, biphenyl or naphthyl groups;

the term "a heteroaryl" means: a 5- to 20-membered, preferably from 4- to 19-membered, more preferably from 4- to 10-membered, aromatic monocyclic or bicyclic group containing at least one heteroatom, preferably from 1 to 3 heteroatoms selected from O, S or N, unless otherwise specified;

Examples of such heteroaryl groups include triazolyl, benzimidazolyl, indolyl, 1,2,4-triazolo[1,5-a]pyrimidinyl, tetrazolyl, furyl, thienyl, pyrrolyl, pyrazoyl, pyrazolyl, imidazolyl, thiazolyl, thiazoyl, oxazolyl, 1-benzofuryl, 1-benzothienyl, indanyl, indazolyl, benzoimidazolyl, benzisoxazolyl, benzisothiazolyl, benzothiazolyl, benzoxazolyl, benzotriazolyl, pyridyl, quinolinyl, pyridazinyl, cinnolinyl, phthalazinyl, pyrimidinyl, quinazolinyl, pyrazinyl, quinoxalinyl, pyridinyl, thiophenyl, dihydrobenzofuranyl, imidazo[1,2-a]pyridinyl, triazinyl, 1,2,4-triazinyl, chromenylium, phenyl, benzyl, [1,3]oxazolo[4,5-b]pyridinyl, pyrido-pyrimidinyl, pyridinyl, imidazo[4,5-b]pyridinyl, benzopyranonyl, pyrimidino-pyridinyl and pyridazino-cyclohexyl. Preferred heteroaryls are triazolyl, benzimidazolyl, indolyl, and 1,2,4-triazolo[1,5-a]pyrimidinyl, imidazo[1,2-a]pyridinyl, benzoxazolyl, pyridazinyl, triazinyl, 1,2,4-triazinyl, [1,3]oxazolo[4,5-b]pyridinyl, pyrido-pyrimidinyl, pyridinyl, imidazo[4,5-b]pyridinyl, benzopyranonyl, pyrimidino-pyridinyl and pyridazino-cyclohexyl;

the term "a heterocycloalkyl" means: a 4- to 10-membered, saturated or partially unsaturated, monocyclic or bicyclic group comprising from one to three heteroatoms selected from O, S or N; the heterocycloalkyl group may be attached to the rest of the molecule via a carbon atom or via a heteroatom; the term bicyclic heterocycloalkyl includes fused bicycles and spiro-type rings.

By way of saturated heterocycloalkyl comprising from 5 to 6 atoms, mention may be made of oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridinyl, dioxanyl, morpholinyl, piperidinyl, piperazinyl, tetrahydrothiopyranyl, dithianyl, thiomorpholinyl or isoxazolidinyl.

When the heterocycloalkyl is substituted, the substitution(s) may be on one (or more) carbon atom(s) and/or on the heteroatom(s). When the heterocycloalkyl comprises several substituents, they may be borne by one and the same atom or different atoms.

The term "substituted" in the present invention means that at least one of the hydrogen atom(s) of said group or radical is replaced with at least one substituent other than H.

When the suffix "ene" is used in conjunction with an alkyl, aryl or heteroaryl group, this means that the alkyl, aryl or heteroaryl group defined above is a divalent radical, i.e. it has two points of attachment to other groups.

The present invention also relates to a compound having the following formula (II):

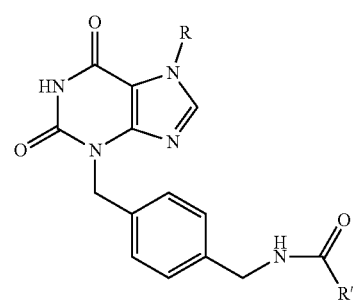

(II)

wherein R and R' are as defined above in formula (I).

Such compounds correspond to compounds of formula (I) wherein Ar is a phenylene group, $X_1$ is CO and R" is H.

The present invention also relates to a compound having the following formula (III):

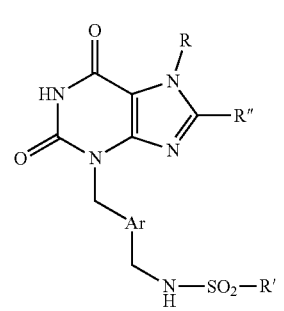

(III)

wherein:
Ar, R, and R" are as defined in formula (I);
R' is chosen from the group consisting of:
  $(C_1-C_6)$alkyl groups, possibly substituted with one or several substituents selected from:
    $(C_5-C_{12})$aryl, optionally substituted by a $(C_1-C_6)$ alkyl group,
    —$OR_a$, $R_a$ being selected from: H, and $(C_1-C_6)$alkyl, $R_a$ being preferably H,
    —$NH_2$,
    —NH—C(=O)—O—$(C_1-C_6)$alkyl, and
    (hetero)cycloalkyl;
  heteroaryl groups,
  possibly substituted with one or several substituents selected from:
    $(C_1-C_6)$alkyl,
    $(C_5-C_{12})$aryl, and
    heteroaryl groups, optionally substituted by a $(C_1-C_6)$alkyl group;
  $(C_5-C_{12})$aryl groups, possibly fused with one heterocycloalkyl or heteroaryl group, optionally substituted with one or several substituents selected from:
    $(C_1-C_6)$alkyl, and $COR_2$, $R_2$ being a $(C_1-C_6)$alkyl group;

said aryl group being possibly substituted with one or several substituents selected from:
  $(C_1-C_6)$alkyl,
  $(C_5-C_{12})$aryl,
  heteroaryl, optionally substituted by a $(C_1-C_6)$alkyl group,
  halogen,
  —$CH_2$-heteroaryl,
  heterocycloalkyl, optionally fused with a phenyl group,
  —$NO_2$,
  $OR_a$, $R_a$ being selected from:
    H,
    $(C_1-C_6)$alkyl,
    $(C_5-C_{12})$aryl, optionally substituted with a substituent chosen from the halo$(C_1-C_6)$alkyl groups, in particular $CF_3$,
    cycloalkyl,
    heteroaryl, optionally substituted with a substituent chosen from the $(C_1-C_6)$alkyl groups, such as methyl,
    heterocycloalkyl, in particular chosen from the $(C_1-C_6)$alkyl groups, such as methyl, and the $(C_1-C_6)$alkylene-$(C_2-C_6)$alkynyl groups, and
    —$CH_2$—$(C_5-C_{12})$aryl,
  —C(=O)—$R_e$, $R_e$ being a heterocycloalkyl,
  —$NR_bR_c$, $R_b$ and $R_c$, being, independently of one another, H or $(C_1-C_6)$alkyl, and $R_b$ and $R_c$, being preferably H, and
  —NHC(=O)$R_d$, $R_d$ being a $(C_1-C_6)$alkyl group.

Such compounds correspond to compounds of formula (I) wherein $X_1$ is $SO_2$.

According to a preferred embodiment, in formula (I) or (III), Ar is a phenylene (—$C_6H_4$-) radical.

According to a preferred embodiment, in formula (I), (II) or (III), R" is H.

According to a preferred embodiment, in formula (I), (II) or (III), R is methyl or ethyl, preferably ethyl.

A preferred group of compounds of the invention consist of compounds of formula (I) wherein Ar is a phenylene radical, R" is H, and R is ethyl.

The present invention also relates to a compound having the following formula (IV):

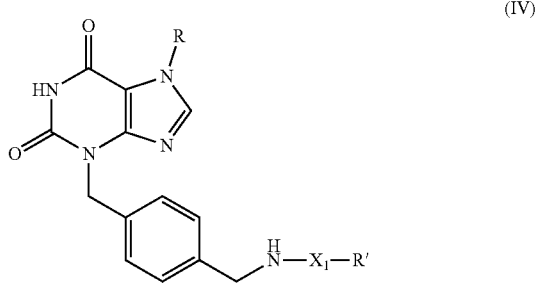

wherein:
R is methyl or ethyl, preferably ethyl, and
$X_1$ and R' are as defined above in formula (I).

Compounds of formula (IV) correspond to compounds of formula (I), wherein R" is H, and Ar is phenylene.

Preferably, in formula (IV), R is ethyl.
Preferably, in formula (IV), R is ethyl and $X_1$ is $SO_2$.
Preferably, in formula (IV), R is ethyl and $X_1$ is CO.

A preferred group of compounds of the invention are compounds having the following formula (IV-1):

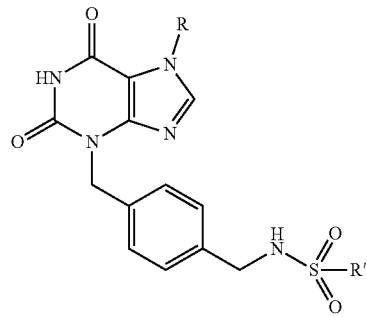

wherein R and R' are as defined above in formula (I).

Compounds of formula (IV-1) correspond to compounds of formula (I) wherein R" is H, Ar is phenylene and $X_1$ is $SO_2$.

Preferably, in formula (IV-1), R is ethyl.

According to a preferred embodiment, in formula (IV-1), R' is a phenyl group, possibly substituted as defined above.

A preferred group of compounds of the invention are compounds of formula (I) wherein R' is a heteroaryl group, preferably a thiophenyl or a benzothiophenyl group, possibly substituted as mentioned above.

A preferred group of compounds of the invention are compounds of formula (IV-1) wherein R' is a heteroaryl group, preferably a thiophenyl or a benzothiophenyl group, possibly substituted as mentioned above.

A preferred group of compounds of the invention are compounds of formula (I) wherein R' is an aryl group, preferably a phenyl group, fused with a heterocycloalkyl group, possibly substituted as mentioned above.

A preferred group of compounds of the invention are compounds of formula (IV-1) wherein R' is an aryl group, preferably a phenyl group, fused with a heterocycloalkyl group, possibly substituted as mentioned above.

A preferred group of compounds of the invention are compounds of formula (I) wherein R' is a biphenyl group, possibly substituted as mentioned above.

A preferred group of compounds of the invention are compounds of formula (IV-1) wherein R' is a biphenyl group, possibly substituted as mentioned above.

A preferred group of compounds of the invention are compounds of formula (I) wherein R' is a phenyl group, possibly substituted as mentioned above.

A preferred group of compounds of the invention are compounds of formula (IV-1) wherein R' is a phenyl group, possibly substituted as mentioned above.

A preferred group of compounds of the invention are compounds of formula (I) wherein R' is a phenyl group, substituted with a heteroaryl group or a —$OR_a$ group, $R_a$ being as defined above.

A preferred group of compounds of the invention are compounds of formula (IV-1) wherein R' is a phenyl group, substituted with a heteroaryl group or a —$OR_a$ group, $R_a$ being as defined above.

A preferred group of compounds of the invention are compounds of formula (I) wherein R' is a phenyl group, substituted with a —$OR_a$ group, $R_a$ being $(C_1-C_6)$alkyl, preferably methyl, $(C_5-C_{12})$aryl, preferably phenyl, and —$CH_2$—$(C_5-C_{12})$aryl, preferably benzyl.

A preferred group of compounds of the invention are compounds of formula (IV-1) wherein R' is a phenyl group, substituted with a —OR$_a$ group, R$_a$ being (C$_1$-C$_6$)alkyl, preferably methyl, (C$_5$-C$_{12}$)aryl, preferably phenyl, and —CH$_2$—(C$_5$-C$_{12}$)aryl, preferably benzyl.

The present invention also relates to a compound having the following formula (V):

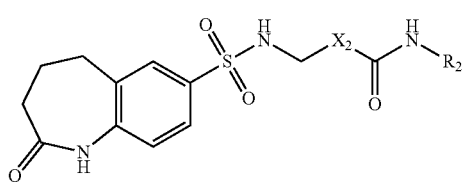

(V)

wherein:
X$_2$ is a cycloalkylene, preferably a cyclohexylene, or phenylene group, and
R$_2$ is a (C$_1$-C$_6$)alkyl group, substituted by a heteroaryl group, said heteroaryl group being optionally substituted by a (C$_1$-C$_6$)alkyl group, or a pharmaceutically acceptable salt and/or tautomeric form thereof, or its racemates, diastereomers or enantiomers.

The present invention also relates to a compound having the following formula (V-1):

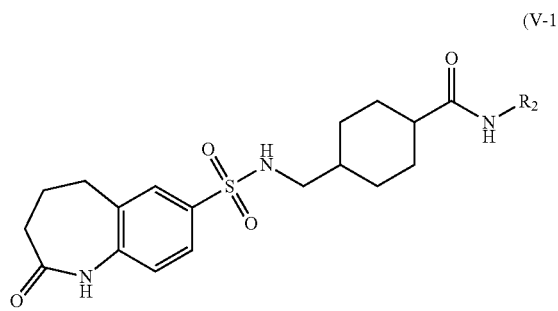

(V-1)

wherein R$_2$ is as defined above in formula (V).

The present invention also relates to a compound having the following formula (V-2):

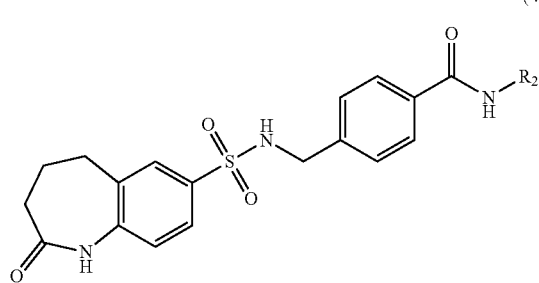

(V-2)

wherein R$_2$ is as defined above in formula (V).

The present invention also relates to a compound of formula (I), (II), (III), (IV), (IV-1), (V), (V-1) or (V-2), as defined above, for use as a medicament.

The present invention also relates to a pharmaceutical composition, comprising a compound of formula (I), (II), (III), (IV), (IV-1), (V), (V-1) or (V-2), as defined above, and also at least one pharmaceutically acceptable excipient.

It is known from the prior art that BET proteins facilitate the assembly of the transcriptional machinery and control gene expression in inflammation, viral infection and cancer biology. It has also been demonstrated that BET proteins are often deregulated in diseases, their transcription-regulating activity being altered and thus affecting numerous growth-promoting genes and cytokines. Recent disclosure of pan-BET inhibitors (multi-targeted BET inhibitors) that attenuate BRD function has allowed the validation of these drug targets, shedding light on their roles in disease.

Therefore, BET protein inhibitors of the present invention, which are xanthine derivative compounds, can be used for treating diseases involving BET proteins. Such diseases are, but are not limited to cancer, inflammatory disease, sepsis, autoimmune disease, neurodegenerative disease, cardiovascular disorder, renal disorder, viral infection or obesity (see patent applications published as US20140296246, EP2646446, WO201580707, US20140296243, EP2859000 and US20150148344).

The present invention also relates to an inhibitor for use in the treatment of cancer, inflammatory disease, sepsis, autoimmune disease, neurodegenerative disease, cardiovascular disorder, renal disorder, viral infection or obesity.

The present invention thus relates to a compound of formula (I), (II), (III), (IV), (IV-1), (V), (V-1) or (V-2), as defined above, for use in the treatment of cancer, inflammatory disease, sepsis, autoimmune disease, neurodegenerative disease, cardiovascular disorder, renal disorder, viral infection, or obesity.

The term "treatment" in the present invention is used herein to characterize a method or process that is aimed at (1) slowing down or stopping the progression, aggravation, or deterioration of the symptoms of the disease; (2) bringing about amelioration of the symptoms of the disease; or (3) curing the disease. A treatment may thus be administered after initiation of the disease, for a therapeutic action.

The present invention also relates to a method for treating a disease involving bromodomains of BET proteins, comprising administering to a patient an effective amount of the inhibitor of general formula (I) as defined above, or of a composition comprising said inhibitor. Such diseases are, but are not limited to cancer, inflammatory disease, sepsis, autoimmune disease, neurodegenerative disease, cardiovascular disorder, renal disorder, viral infection or obesity.

Preferably, the inhibitor is an inhibitor of the BRD4 protein wherein said inhibitor binds to BD1 of BRD4.

Preferably, the inhibitor is an inhibitor of the BRD3 protein wherein said inhibitor binds to BD1 of BRD3.

Preferably, said inhibitor has an IC$_{50}$ for BRD4 (BD1) equal to or less than 50 µM, preferably less than 10 µM, even less than 5 µM, and even preferably less than 1 µM.

The term "IC$_{50}$" in the present invention refers to the half maximal inhibitory concentration which is a measure of the effectiveness of a compound in inhibiting biological function, e.g. inhibition of protein-protein interaction. Typically IC$_{50}$ is measured by homogeneous time resolved fluorescence (HTRF). In the present invention, IC$_{50}$ is determined for a specific BET protein.

In a particular embodiment, the present invention provides a method for treating a patient having a cancer, inflammatory disease, sepsis, autoimmune disease, neurodegenerative disease, cardiovascular disorder, renal disorder, viral infection or obesity condition.

In another embodiment, the disease to be treated is selected from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors. Solid tumors are, but not limited to, tumors of the colon, rectum, prostate, lung, pancreas, liver, kidney, cervix, stomach, ovaries, breast, skin, brain, meninges or central nervous system.

EXAMPLES

Figure 1:
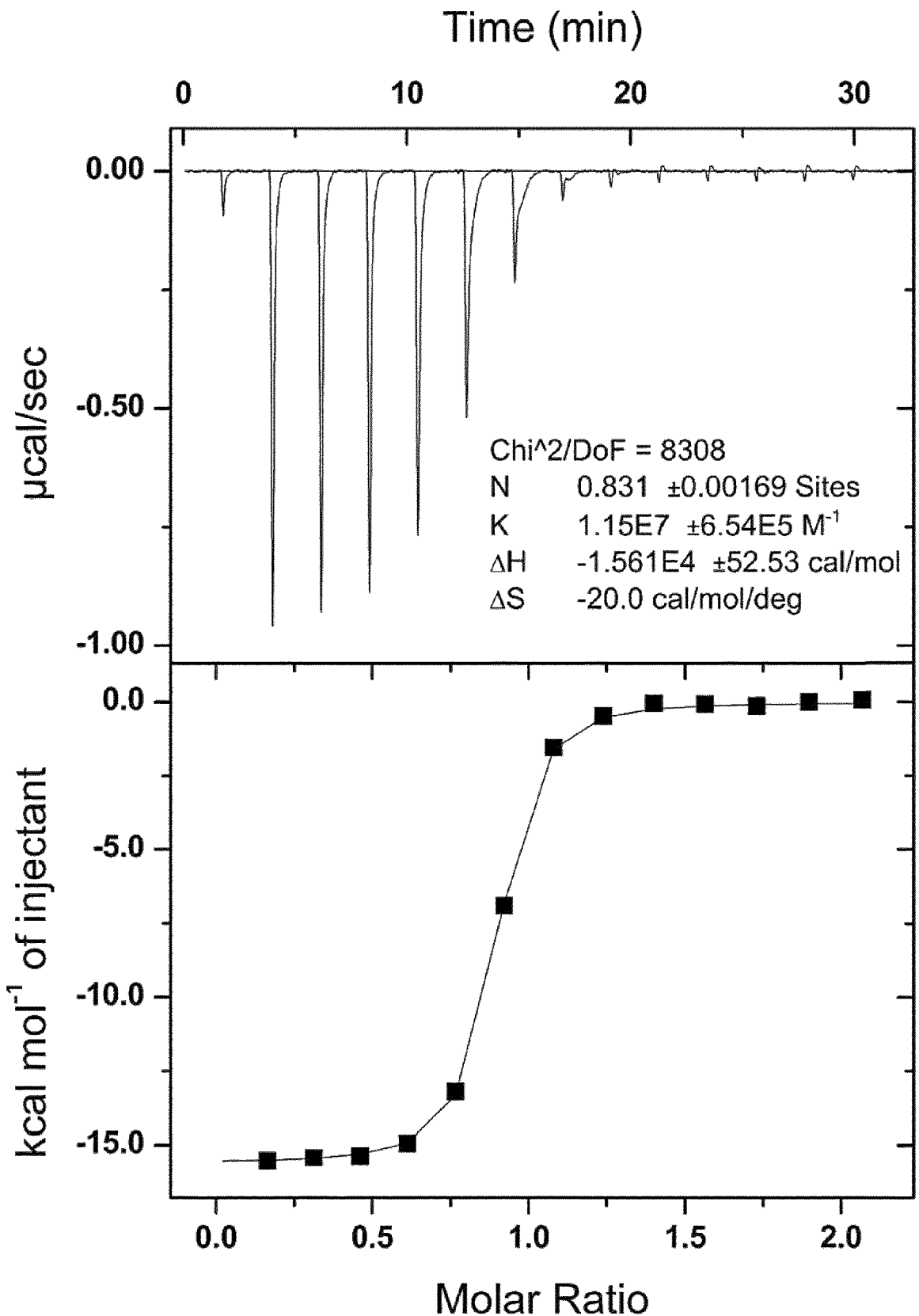
FIG. 1. Isothermal Titration Calorimetry (ITC) of 43c. Thermogram (top) and non-linear least squares fit model of the integrated data (bottom) at 15° C. of Brd4 (BD1) (200 µM in the cell) vs 43c (20 µM in the syringe) as a function of the molar ratio of ligand to the protein.

Preparation of the Compounds According to the Invention

The compounds of the invention can be prepared from commercially available aminoacids or from N-protected (4-(bromomethyl)aryl)methanamines according to procedures described in following schemes 1 and 2 respectively.

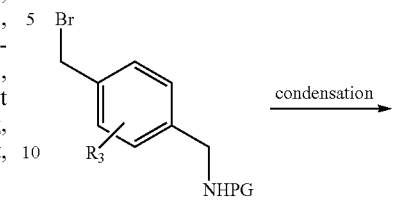

Scheme 2 Synthesis of compounds of the invention from N-protected (4-bromomethyl)aryl)methanamines Scheme 1 Synthesis of compounds of the invention from aminoacids

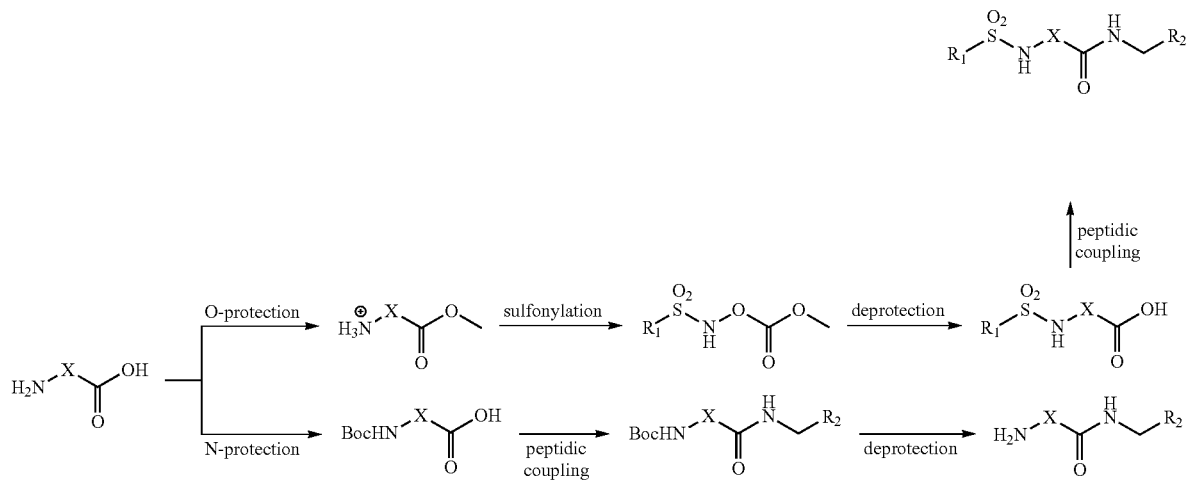

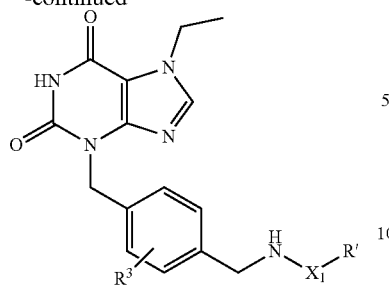

Starting from aminoacids, O-protection reaction followed by sulfonylation with corresponding sulfonyl chlorides, commercially available or self-prepared, affords corresponding methylester sulfonamides. Deprotection and subsequent amidation by various alkyl amines lead to the expected compounds of the invention of the formula 1c-18b. Compounds of the formula 18c-19a can be prepared from trans-4-aminomethyl cyclohexane carboxylic acid using a sequence of N-protection, peptidic coupling and deprotection.

From N-protected (4-(bromomethyl)aryl)methanamines (scheme 2) the various sulfonamides and amides can be synthesized by a condensation with 7-ethyl-1H-purine-2,6(3H,7H)-dione prepared by the typical procedure (WO2017114843(A1) followed by removal of the N-protecting group and sulfonylation/acylation of free amino-group with various sulfonyl chlorides, carboxylic acids and acyl chlorides.

N-protected (4-(bromomethyl)aryl) can be prepared by three different procedures, i) for compound of formula 19c-31b, 33a-42b from commercially available 4-(aminomethyl)benzoic acid through a sequence of reduction, nucleophilic substitution and Boc-protection reactions according to the scheme 3, ii) for the derivative of formula 31c from commercially available 1-methylnaphthalene through a sequence of radical bromination, protection by phtalimide and bromomethylation reactions according to the scheme 4, iii) for the derivative of formula 32a from commercially available 1,4-dimethoxybenzene through a sequence of bromomethylation and protection reactions according to the scheme 5.

Scheme 3 Synthesis of tert-butyl (4-(bromemethyl)benzyl)carbamate

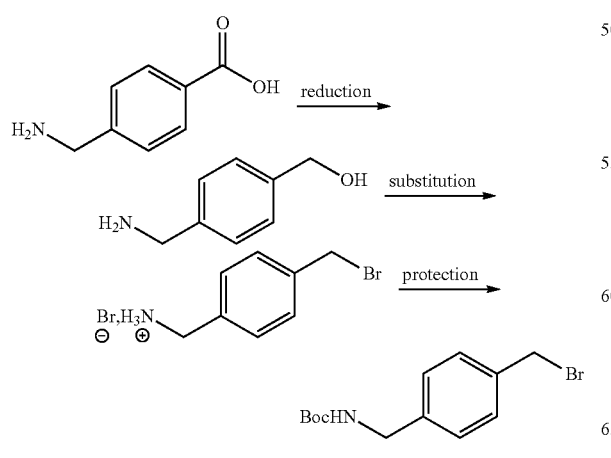

Scheme 4 Synthesis of 2-((4-bromomethyl)napthalen-1-yl)methyl)isoindoline-1,3-dione

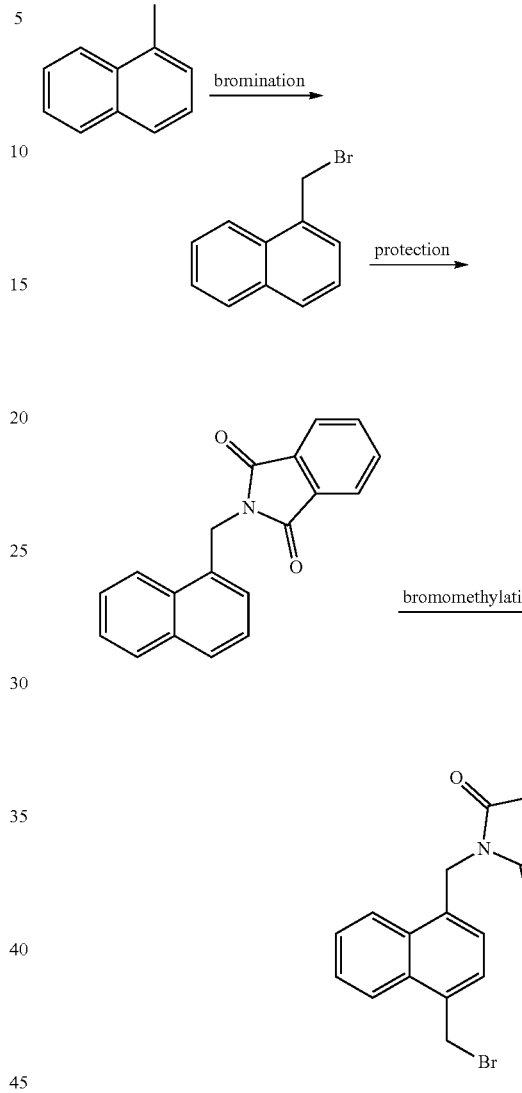

Scheme 5
Synthesis of 2-(4-(bromomethyl)-2,5 dimethoxybenzyl)isoindoline-1,3-dione

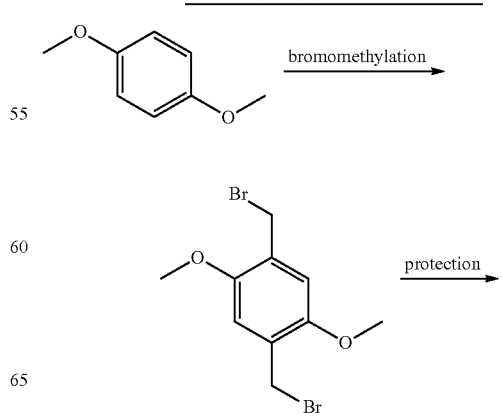

-continued

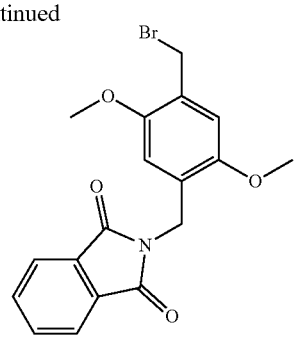

Sulfonamide derivatives of formula 32b-c can be prepared according to the sequence described below (scheme 6). Sulfonylation of 4-(aminomethyl)benzyl alcohol followed by nucleophilic substitution of the hydroxyl group by chloride leads to an intermediate which affords the expected derivatives through a condensation with N3-unsubstituted purine derivative prepared by debenzylation reaction from purines previously described in WO2017114843.

A sulfonamide and amide chemical library of compounds of invention was generated using a sulfonylation or acylation reactions and a collection of building blocks. About 60 building blocks were purchased to prepare a representative set of compounds from the top 1%. The compounds have been synthetized using an automated robotic platform from Chemspeed by coupling previously described 3-(4-(aminomethyl)benzyl)-7-ethyl-1H-purine-2,6(3H,7H)-dione with appropriate commercially available partner for sulfonylation or acylation (scheme 7). The Accelerator Synthetizer SLT100 allows the efficient synthesis of the focused library in 96 well plates that can be directly transferred to a Labcyte Access/Echo® Laboratory Workstation to assess the compounds for their ability to disrupt bromodmain/histone complexes using the homogeneous time-resolved fluorescence (HTRF®) technology ($IC_{50}$ μM).

Scheme 6 Synthesis of sulfonamide derivatives of formula 32b-c

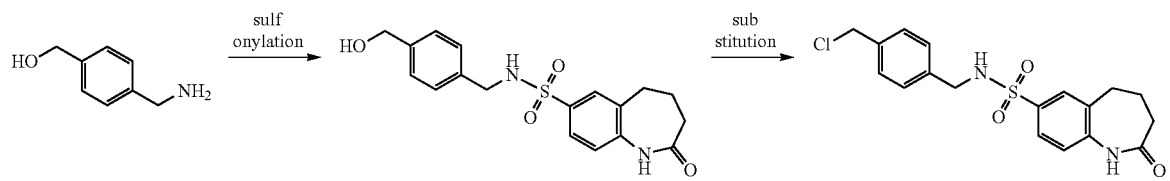

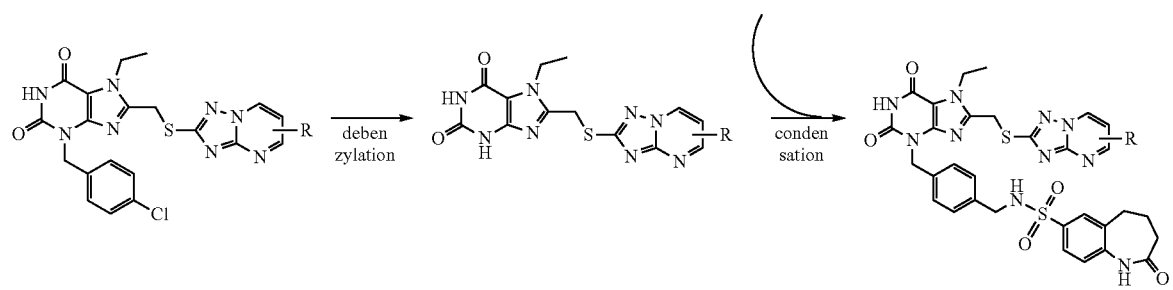

Design and synthesis of compounds of the invention of formula 20b to 31b, 33a to 42b combines molecular modeling coupled to an automated synthesis robotic platform and a high throughput laboratory workstation (referred as DOTS). The in silico optimization strategy relies on 2 main steps, i) the design of a diversity-oriented target-focused chemical library using medicinal chemistry relevant reactions and a collection of commercially available building blocks ii) the virtual screening of this chemical library using S4MPLE, a conformational sampling tool, able to deal with hundreds of intra/intermolecular degrees of freedom in the context of one (conformer enumeration) or more molecules (docking). S4MPLE relies on a Lamarckian genetic algorithm and significant flexibility may be enabled (e.g. ligands, target side chains and backbone). Energy calculations are based on the AMBER force field and its generalized version GAFF for ligands.

Scheme 7:
Synthesis of bromodomain inhibitor of formula 20b-31b, 33a-42b

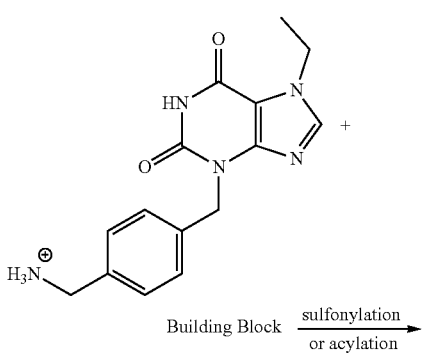

Building Block $\xrightarrow{\text{sulfonylation or acylation}}$

-continued

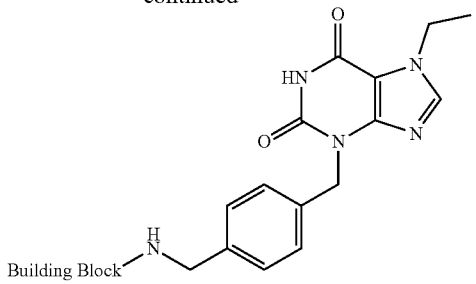

Building Block

Although the exemplary embodiments of the present invention have been disclosed for illustrative purposes, a person skilled in the art will appreciate that various modifications, additions and substitutions are possible, without departing from the scope and spirit of the invention as disclosed in the accompanying claims. The present invention will now be illustrated using the following examples and figures, which are given by way of illustration, and are in no way limiting.

General Synthesis of the Compounds According to the Invention

Commercially available reagents were used without additional purification. Column chromatography was performed using Macherey-Nagel Kieselgel 60 (70-230 mesh). The petroleum spirit refers to the fraction with distillation range 40-70° C. $^1$H and $^{13}$C NMR spectra were recorded at room temperature in DMSO-d6, CD$_3$OD or CDCl$_3$ by using a Bruker AC400, AC250 or Agilent DD2 400 spectrometers. Chemical shifts (δ) are reported in parts per million (ppm) with internal reference TMS and coupling values (J) in hertz. Abbreviations for peaks are, br: broad, s: singlet, d: doublet, t: triplet, q: quadruplet, quint: quintuplet, sex: sextuplet and m: multiplet. The spectra recorded are consistent with the proposed structures. Reaction monitoring and purity of compounds were recorded by using analytical Agilent Infinity high performance liquid chromatography (Column Zorbax SB-C18 1.8 μM (2.1×50 mm); Mobile phase (A: 0.1% FA H$_2$O, B: 0.1% FA MeCN, Time/% B 0/10, 4/90, 7/90, 9/10, 10/10); Flow rate 0.3 mL/min; Diluent MeCOH) with DAD at 230 nM. All tested compounds yielded data consistent with a purity of ≥95%.

Example 1: 4-((2-oxo-2,3,4,5-tetrahydro-1H-benzo[b]azepine-7-sulfonamido)methyl)-N-(2-(thiophen-2-yl)ethyl)cyclohexanecarboxamide (5b)

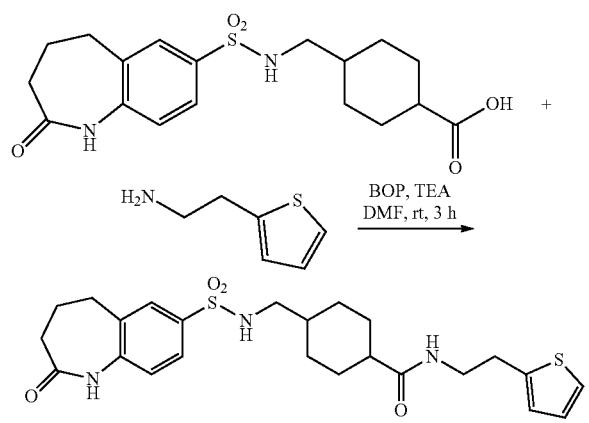

To a solution of 3b (50 mg, 0.13 mmol) in dimethylformamide (2 mL) were added BOP reagent (58 mg, 0.13 mmol) and 2-thiophenethylamine (15 μL, 0.13 mmol). The mixture was stirred at room temperature for 10 min and triethylamine (36 μL, 0.26 mmol) was injected. The resulting mixture was stirred at room temperature for 3 hours, then dimethylformamide was removed under reduced pressure. The residue was suspended in H$_2$O (5 mL), the precipitate collected by filtration was generously washed with H$_2$O and dried under reduced pressure to afford 4-((2-oxo-2,3,4,5-tetrahydro-1H-benzo[b]azepine-7-sulfonamido)methyl)-N-(2-(thiophen-2-yl)ethyl)cyclohexanecarboxamide 5b (51 mg, 80%) as a light-beige powder. $^1$H NMR (250 MHz, CD$_3$OD) δ 7.78-7.67 (m, 2H), 7.17 (dd, J=9.9, 6.7 Hz, 2H), 6.96-6.88 (m, 1H), 6.84 (d, J=2.6 Hz, 1H), 3.39 (dd, J=8.8, 5.0 Hz, 2H), 2.99 (t, J=6.9 Hz, 2H), 2.86 (t, J=6.6 Hz, 2H), 2.70 (d, J=6.7 Hz, 2H), 2.38-2.20 (m, 4H), 2.07 (t, J=12.2 Hz, 1H), 1.78 (d, J=10.1 Hz, 4H), 1.38 (dd, J=23.6, 11.2 Hz, 3H), 0.91 (q, J=12.5 Hz, 2H). $^{13}$C NMR (101 MHz, DMSO-d6+CD$_3$OD) δ 177.83, 175.76, 143.37, 142.45, 138.00, 135.73, 129.17, 127.66, 127.01, 126.03, 124.51, 122.70, 49.74, 45.61, 41.43, 38.11, 33.74, 31.05, 30.48 (×2), 30.15, 29.71 (×2), 29.05. LCMS C$_{24}$H$_{31}$N$_3$O$_4$S$_2$ Rt=5.950, m/z=489.6, purity >95%.

4-((2-oxo-2,3,4,5-tetrahydro-1H-benzo[b]azepine-7-sulfonamido)methyl) cyclohexanecarboxylic acid (3b)

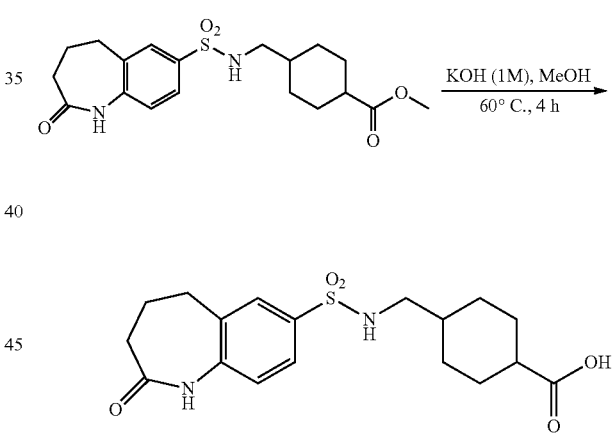

A solution of 1c (1 g, 2.54 mmol) in methanol (60 mL) was treated with 1M aqueous solution of potassium hydroxide (1.4 g, 25.4 mmol) and the resulting mixture was stirred at 60° C. for 4 hours. The mixture was allowed to cool down to room temperature and 30 mL of 1M solution of hydrochloric acid were added. A precipitate formed was filtered off, generously washed with H$_2$O and dried under reduced pressure to afford 4-((2-oxo-2,3,4,5-tetrahydro-1H-benzo[b]azepine-7-sulfonamido)methyl) cyclohexanecarboxylic acid 3b (780 mg, 81%) as a white solid. $^1$H NMR (250 MHz, CD$_3$OD) δ 7.73 (dd, J=9.9, 1.5 Hz, 2H), 7.17 (d, J=8.1 Hz, 1H), 2.87 (t, J=6.6 Hz, 2H), 2.71 (d, J=6.7 Hz, 2H), 2.39-2.09 (m, 5H), 1.96 (d, J=11.2 Hz, 2H), 1.80 (d, J=11.0 Hz, 2H), 1.45-1.21 (m, 3H), 0.92 (qd, J=12.9, 3.0 Hz, 2H). $^{13}$C NMR (63 MHz, CD$_3$OD) δ 176.72 (×2), 143.66, 138.81, 136.31, 129.57, 127.43, 123.13, 50.11, 44.44, 38.65, 34.01, 31.46, 30.77 (×2), 29.79 (×2), 29.36.

Methyl 4-((2-oxo-2,3,4,5-tetrahydro-1H-benzo[b]azepine-7-sulfonamido)methyl)cyclohexanecarboxylate (1c)

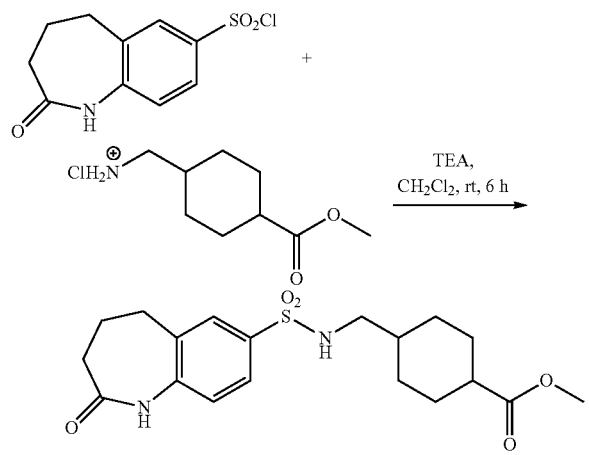

To a suspension of methyl 4-(aminomethyl)cyclohexanecarboxylate hydrochloric salt (660 mg, 3.18 mmol) in dichloromethane (25 mL) were added triethylamine (2.2 mL, 15.9 mmol) and 1b (825 mg, 3.18 mmol), and the resulting mixture was stirred at room temperature for 6 hours. Then the reaction mixture was washed twice with 1M solution of HCl (30 mL) and NaHCO$_3$ (30 mL). An organic layer was dried over Na$_2$SO$_4$ and concentrated under reduced pressure to afford methyl 4-((2-oxo-2,3,4,5-tetrahydro-1H-benzo[b]azepine-7-sulfonamido)methyl)cyclohexanecarboxylate 1c (1.25 g, 99%) as a white solid. $^1$H NMR (250 MHz, CD$_3$OD+CDCl$_3$) δ 7.68 (dd, J=6.0, 3.3 Hz, 2H), 7.11 (d, J=8.8 Hz, 1H), 3.63 (s, 3H), 2.83 (t, J=6.4 Hz, 2H), 2.70 (d, J=6.7 Hz, 2H), 2.40-2.09 (m, 5H), 1.94 (d, J=12.4 Hz, 2H), 1.81 (d, J=11.1 Hz, 2H), 1.47-1.22 (m, 3H), 0.90 (dt, J=12.2, 10.1 Hz, 2H). $^{13}$C NMR (63 MHz, CD$_3$OD+CDCl$_3$) δ 177.32, 176.09, 142.70, 137.79, 135.47, 129.05, 126.86, 122.51, 51.82, 49.47, 43.74, 37.86, 33.50, 31.03, 30.06 (×2), 28.93 (×2), 28.71.

Methyl 4-(aminomethyl)cyclohexanecarboxylate hydrochloric salt

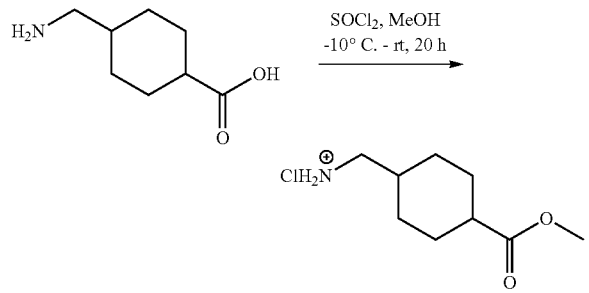

Thionyl chloride (763 μl, 10.5 mmol) was injected dropwise over 10 min to 5 mL of anhydrous MeOH at −10° C. To this solution was added 4-(aminomethyl)cyclohexanecarboxylic acid (500 mg, 3.18 mmol) at the same temperature, and the resulting mixture was stirred at room temperature for 20 hours. The solvent was removed under reduced pressure to afford methyl 4-(aminomethyl)cyclohexanecarboxylate hydrochloric salt (660 mg, 100%) as a yellowish solid. $^1$H NMR (250 MHz, CD$_3$OD) δ 3.66 (s, 3H), 2.80 (d, J=6.6 Hz, 2H), 2.41-2.23 (m, 1H), 2.03 (d, J=12.0 Hz, 2H), 1.89 (d, J=11.9 Hz, 2H), 1.64 (s, 1H), 1.54-1.34 (m, 2H), 1.18-0.99 (m, 2H). $^{13}$C NMR (63 MHz, CD$_3$OD) δ 177.61, 52.07, 46.36, 43.99, 36.69, 30.27 (×2), 29.26 (×2).

2-Oxo-2,3,4,5-tetrahydro-1H-benzo[b]azepine-7-sulfonyl chloride (1b)

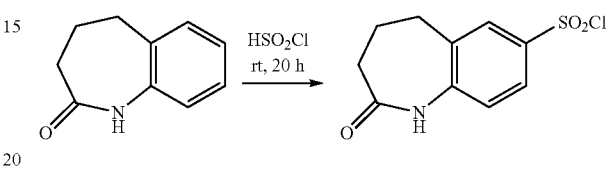

Under argon, chlorosulfonic acid (7.22 mL, 109.8 mmol) was added dropwise under rigorous stirring to 1a (1.77 g, 11 mmol), and the resulting mixture was stirred at room temperature for 20 hours. The flask was cooled down and cold H$_2$O was added dropwise until a white precipitate was formed. The precipitate was filtered, carefully washed with cold H$_2$O and dried under vacuum to afford 2-oxo-2,3,4,5-tetrahydro-1H-benzo[b]azepine-7-sulfonyl chloride 1b (2.1 g, 75%) as a white powder. $^1$H NMR (400 MHz, DMSO) δ 9.56 (s, 1H), 7.47 (d, J=1.8 Hz, 1H), 7.43 (dd, J=8.1, 2.0 Hz, 1H), 6.90 (d, J=8.1 Hz, 1H), 2.67 (t, J=6.7 Hz, 2H), 2.17-2.05 (m, 4H). $^{13}$C NMR (101 MHz, DMSO) δ 173.36, 144.17, 139.27, 132.89, 127.10, 124.58, 120.79, 33.00, 29.99, 28.02.

4,5-dihydro-1H-benzo[b]azepin-2(3H)-one (1a)

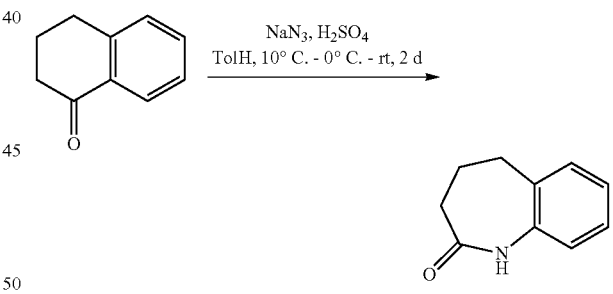

To a solution of a-tetralone (5 g, 34.2 mmol) in toluene (40 mL) NaN$_3$ (8.9 g, 137 mmol) was added at 10° C. and a mixture was cooled to 0° C. followed by injection of H$_2$SO$_4$ conc (16 mL). The reaction mixture was stirred at room temperature for 2 days. The solid obtained was filtered off and generously washed with toluene, dissolved in a mixture of EtOAc and H$_2$O and extracted with EtOAc (20 mL×3). An organic layer was washed with NaCl, dried over Na$_2$SO$_4$ and the solvent was removed under reduced pressure to afford 4,5-dihydro-1H-benzo[b]azepin-2(3H)-one 1a (5.1 g, 93%) as light yellow crystals. $^1$H NMR (400 MHz, DMSO-d6) δ 9.51 (s, 1H), 7.28-7.17 (m, 2H), 7.07 (t, J=7.4 Hz, 1H), 6.95 (d, J=7.8 Hz, 1H), 2.66 (t, J=6.6 Hz, 2H), 2.19-2.02 (m, 4H). $^{13}$C NMR (101 MHz, DMSO-d6) δ 173.58, 138.95, 133.82, 129.80, 127.31, 124.85, 121.72, 32.94, 29.98, 28.17.

Example 2: 4-(aminomethyl)-N-(2-(thiophen-2-yl) ethyl) cyclohexanecarboxamide hydrochloric salt (8b)

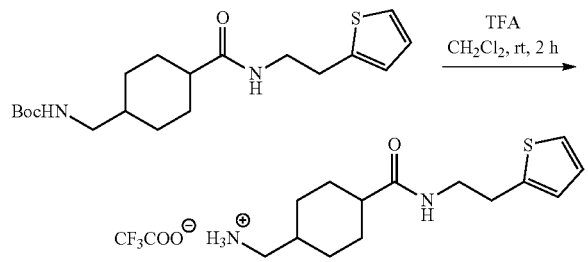

A solution of 18c (50 mg, 0.14 mmol) in dichloromethane (1 mL) was treated with trifluoroacetic acid (104 µL, 1.4 mmol) and the resulting mixture was stirred at room temperature for 2 hours. Then the solvent was removed under reduced pressure, a residue was dissolved in H$_2$O and washed with EtOAc (10 mL×3). Combined organic layers were dried over Na$_2$SO$_4$ and concentrated under reduced pressure to afford 4-(aminomethyl)-N-(2-(thiophen-2-yl) ethyl)cyclohexane-carboxamide hydrochloric salt 8b (35 mg, yield 66%) as a beige solid. $^1$H NMR (250 MHz, CD$_3$OD) δ 7.19 (dd, J=5.1, 1.0 Hz, 1H), 6.91 (dd, J=5.1, 3.5 Hz, 1H), 6.88-6.81 (m, 1H), 3.40 (t, J=7.0 Hz, 2H), 3.00 (t, J=7.0 Hz, 2H), 2.78 (d, J=7.0 Hz, 2H), 2.16 (tt, J=12.0, 3.2 Hz, 1H), 1.95-1.77 (m, 4H), 1.72-1.57 (m, 1H), 1.47 (ddd, J=15.9, 13.5, 3.7 Hz, 2H), 1.15-0.95 (m, 2H). $^{13}$C NMR (63 MHz, CD$_3$OD) δ 178.73, 178.64, 142.55, 127.82, 126.31, 124.65, 46.17, 45.71, 41.97, 36.69, 30.44, 30.31 (×2), 29.72 (×2). LCMS C$_{14}$H$_{22}$N$_2$OS Rt=7.321, m/z=266.8, purity 100%.

Tert-butyl ((4-((2-(thiophen-2-yl)ethyl)carbamoyl) cyclohexyl)methyl) carbamate (18c)

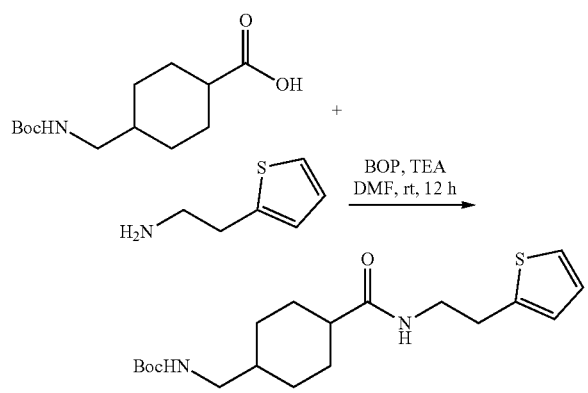

To a solution of 4-(((tert-butoxycarbonyl)amino)methyl) cyclohexanecarboxylic acid (158 mg, 0.61 mmol) in dimethylformamide (6 mL) were added BOP reagent (271.4 mg, 0.61 mmol) and 2-aminoethylthiophene (71.9 µL, 0.61 mmol). The reaction mixture was stirred at room temperature for 10 min and triethylamine (213.7 µL, 1.53 mmol) was injected. The resulting mixture was stirred at room temperature for 12 hours, then dimethylformamide was removed under reduced pressure. The residue was suspended in H$_2$O (3 mL), the precipitate collected by filtration was generously washed with H$_2$O and dried under reduced pressure to afford tert-butyl ((4-((2-(thiophen-2-yl)ethyl)carbamoyl)cyclohexyl)methyl)carbamate 18c (199 mg, 89%) as a white solid. $^1$H NMR (250 MHz, CD$_3$OD) δ 7.20 (dd, J=5.1, 1.0 Hz, 1H), 6.92 (dd, J=5.1, 3.5 Hz, 1H), 6.85 (d, J=2.5 Hz, 1H), 3.40 (t, J=7.0 Hz, 2H), 3.00 (t, J=6.9 Hz, 2H), 2.88 (d, J=6.7 Hz, 2H), 2.10 (t, J=12.2 Hz, 1H), 1.80 (d, J=11.2 Hz, 4H), 1.51-1.33 (m, 12H), 0.95 (dd, J=22.7, 12.2 Hz, 2H). $^{13}$C NMR (63 MHz, CD$_3$OD) δ 179.21, 158.71, 142.56, 127.81, 126.31, 124.65, 79.88, 47.47, 46.40, 41.96, 39.07, 30.90, 30.44 (×3), 30.17 (×2), 28.77 (×2).

4-(((tert-butoxycarbonyl)amino)methyl)cyclohexanecarboxylic acid

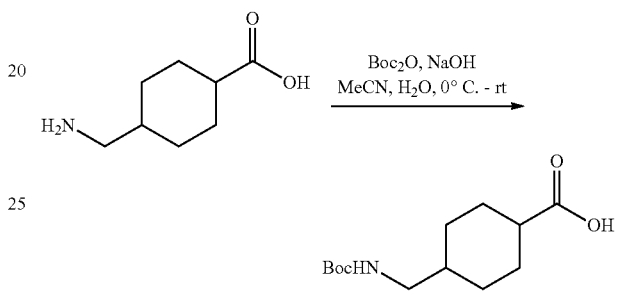

To 1M aqueous solution of NaOH (45.8 mg, 1.15 mmol) cooled in an ice bath was added trans-4-aminomethyl cyclohexane carboxylic acid (100 mg, 0.64 mmol). The solution was diluted with MeCN to 1 mL. Di-tert-butyl dicarbonate (175 mg, 0.81 mmol) was added portion wise, and the mixture was stirred at room temperature overnight. Solvents were removed under reduced pressure, and the residue was dissolved in H$_2$O (2 mL). NaHSO$_4$ was added to pH=3 and the mixture was extracted with EtOAc (5 mL×3), combined organic layers were dried over Na$_2$SO$_4$ and concentrated under reduced pressure to afford 4-(((tert-butoxycarbonyl) amino)methyl)cyclohexanecarboxylic acid (160 mg, 98%) as a white solid. $^1$H NMR (250 MHz, CD$_3$OD) δ 2.89 (t, J=6.1 Hz, 2H), 2.20 (dd, J=13.9, 10.5 Hz, 1H), 1.99 (d, J=13.3 Hz, 2H), 1.81 (d, J=11.1 Hz, 2H), 1.49-1.29 (m, 12H), 0.96 (dd, J=24.9, 10.3 Hz, 2H). $^{13}$C NMR (63 MHz, CD$_3$OD) δ 179.97, 158.70, 79.82, 47.46, 44.54, 39.13, 30.87 (×3), 29.89 (×2), 28.78 (×2).

Example 3: N-(4-((7-ethyl-2,6-dioxo-1,2,6,7-tetrahydro-3H-purin-3-yl)methyl)benzyl)-4-phenoxybenzenesulfonamide (30c)

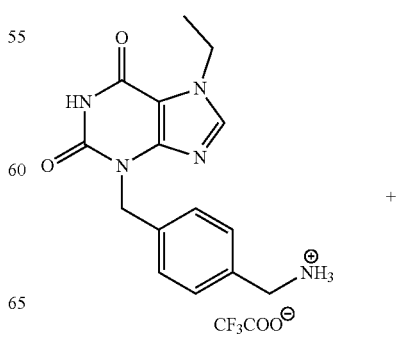

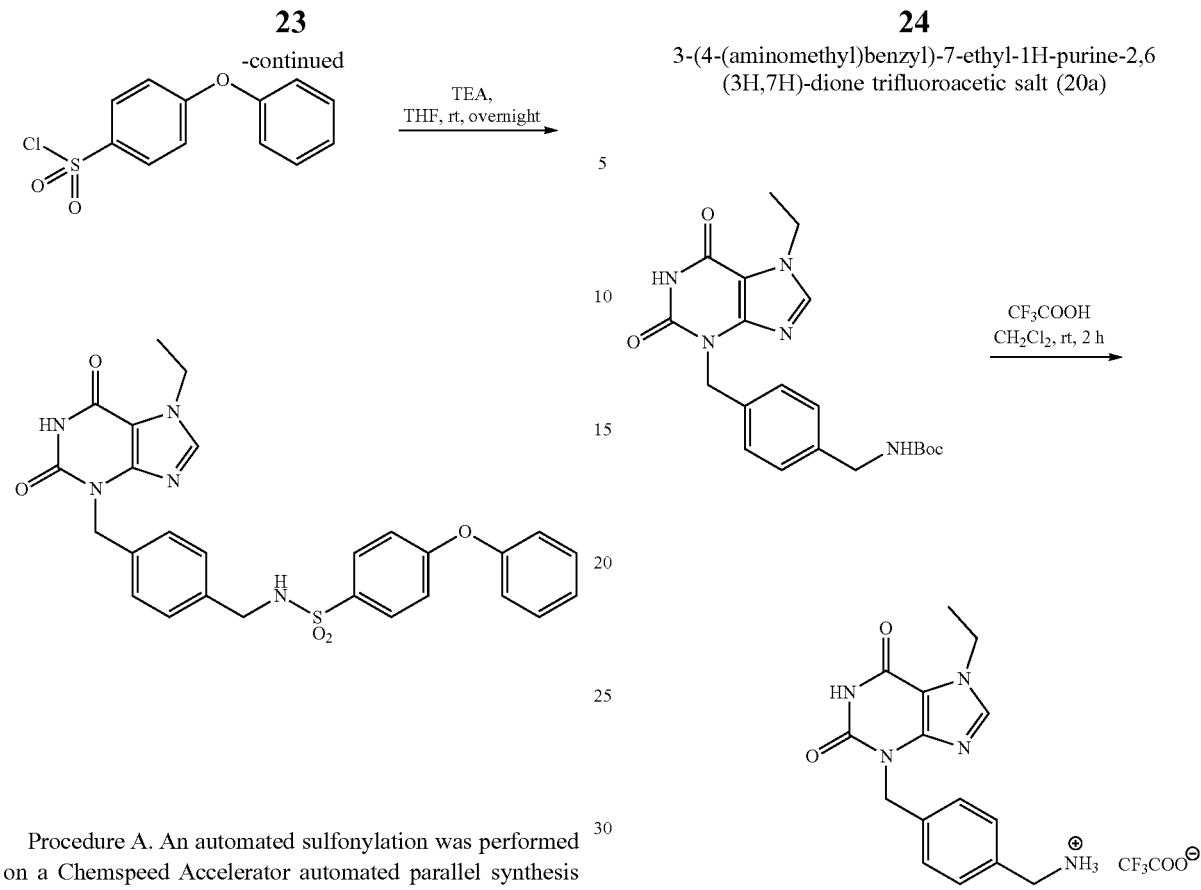

3-(4-(aminomethyl)benzyl)-7-ethyl-1H-purine-2,6 (3H,7H)-dione trifluoroacetic salt (20a)

Procedure A. An automated sulfonylation was performed on a Chemspeed Accelerator automated parallel synthesis platform. The reactions were run in 2 mL LC glass vials. A stock solution of 3-(4-(aminomethyl)benzyl)-7-ethylxanthine trifluoroacetic salt (206.5 mg, 1 eq) and trietylamine (138.7 µL, 2 eq) in anhydrous tetrahydrofurane (20 mL) was prepared and placed on the robotic deck. The robot automatically prepared the reaction mixtures by dispensing the prepared solution (400 µL) to the individual vials containing chlorosulfonyl derivatives (0.01 mmol) via the liquid handling tool. After 12 hours at room temperature samples were taken out and analyzed by LCMS to determine the percent of conversion. The product solutions were concentrated at 80° C., and residues were diluted with dimethylsulfoxide to afford a solution 5.10-2M of the expected compounds. Further LCMS analysis allowed rectifying the final concentration of the products precisely to 10-2M for further biological evaluations.

Procedure B. To a solution of 20a (50 mg, 0.12 mmol) in tetrahydrofurane (5 mL) were injected triethyamine (84.5 µL, 0.60 mmol) and 4-phenoxybenzenesulfonyl chloride (32.2 mg, 0.12 mmol), and the resulting mixture was stirred at room temperature overnight. The solvent was removed under reduced pressure, and a crude product was purified by column chromatography (eluent 20:1, $CH_2Cl_2$:MeOH) to afford N-(4-((7-ethyl-2,6-dioxo-1,2,6,7-tetrahydro-3H-purin-3-yl)methyl)benzyl)-4-phenoxybenzenesulfonamide 30c (54.8 mg, 86%) as a white solid. $^1$H NMR (250 MHz, $CD_3OD$) δ 7.89 (s, 1H), 7.69 (d, J=9.0 Hz, 2H), 7.42 (dd, J=8.2, 7.5 Hz, 2H), 7.29 (d, J=8.2 Hz, 2H), 7.25-7.17 (m, 1H), 7.11 (d, J=8.3 Hz, 2H), 7.06-6.99 (m, 2H), 6.93 (d, J=8.9 Hz, 2H), 5.13 (s, 2H), 4.25 (q, J=7.1 Hz, 2H), 4.02 (s, 2H), 1.44 (t, J=7.2 Hz, 3H). LCMS $C_{27}H_{25}N_5O_5S$ Rt=6.594, m/z=531.6, purity>96%.

A suspension of 19c (200 mg, 0.50 mmol) in dichloromethane (3 mL) was treated with trifluoroacetic acid (450 µl), and the resulting mixture was stirred at room temperature for 1 hour. The solvent was removed under reduced pressure, and a crude product was purified by column chromatography (eluent 6:1:0.1, $CH_2Cl_2$:MeOH:$NH_3$) to afford 3-(4-(aminomethyl)benzyl)-7-ethyl-1H-purine-2,6 (3H,7H)-dione trifluoroacetic salt 20a (207 mg, 100%) as a white solid. $^1$H NMR (250 MHz, $CD_3OD$) δ 7.96 (s, 1H), 7.51 (d, J=8.2 Hz, 2H), 7.42 (d, J=8.2 Hz, 2H), 5.26 (s, 2H), 4.36 (q, J=7.2 Hz, 2H), 4.10 (s, 2H), 1.51 (t, J=7.2 Hz, 3H). 13C NMR (63 MHz, $CD_3OD$) δ 156.49, 152.88, 151.55, 143.21, 139.18, 133.97, 130.15 (×2), 129.78 (×2), 108.50, 46.22, 44.01, 43.42, 16.78.

Tert-butyl 4-((7-ethyl-2,6-dioxo-1H-purin-3(2H,6H,7H)-yl)methyl)benzylcarbamate (19c)

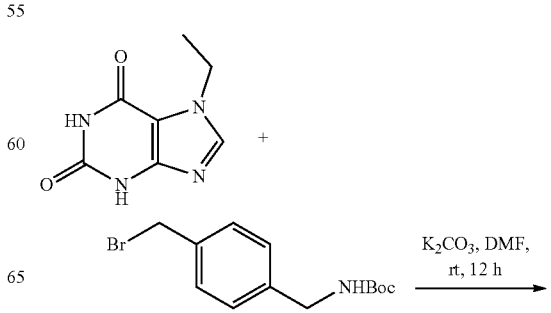

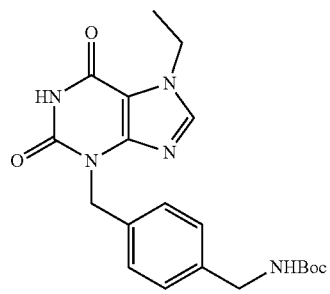

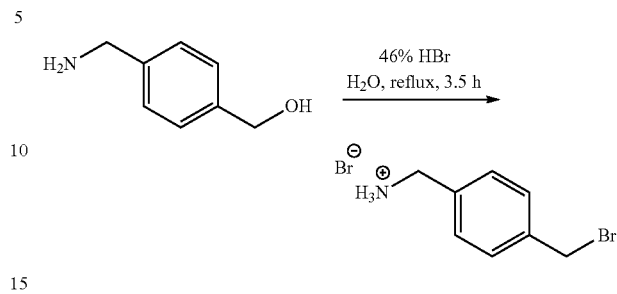

(4-(bromomethyl)phenyl)methanamine hydrobromic salt

To a suspension of 7-ethyl-1H-purine-2,6(3H,7H)-dione (180 mg, 1 mmol) and K$_2$CO$_3$ (151.8 mg, 1.1 mmol) in dimethylformamide (15 mL) tert-butyl 4-(bromomethyl)benzylcarbamate (300 mg, 1 mmol) was added portionwise, and the resulting mixture was stirred at room temperature overnight. The solvent was removed under reduced pressure, and a crude product was purified by column chromatography (eluent 40:1:0.1 CH$_2$Cl$_2$:MeOH:NH$_3$) to afford 4-((7-ethyl-2,6-dioxo-1H-purin-3(2H,6H,7H)-yl)methyl)benzylcarbamate 19c (202 mg, 51%) as a white solid. $^1$H NMR (250 MHz, DMSO-d6) δ 8.07 (s, 1H), 7.30 (d, J=8.1 Hz, 2H), 7.18 (d, J=8.1 Hz, 2H), 5.09 (s, 2H), 4.25 (q, J=7.1 Hz, 2H), 4.09 (d, J=6.0 Hz, 2H), 1.47-1.31 (m, 12H). $^{13}$C NMR (63 MHz, DMSO-d6) δ 155.78, 154.65, 150.83, 149.72, 141.99, 139.36, 135.43, 127.58 (×2), 127.01 (×2), 106.49, 77.79, 44.55, 43.10, 41.57, 28.27 (×3), 16.26.

Tert-butyl 4-(bromomethyl)benzylcarbamate

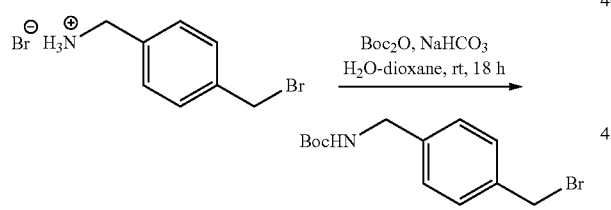

To the solution of (4-(bromomethyl)phenyl)methanamine hydrobromic salt (1 g, 5 mmol) in a mixture of H$_2$O and dioxane (40 mL, 1:1), di-tert-butyl dicarbonate (3.3 g, 15 mmol) was added at 0° C. Then NaHCO$_3$ (0.87 g, 10 mmol) was added at the same temperature, and the resulting mixture was stirred for 3 hours at room temperature. The mixture was extracted with Et$_2$O (×3), combined organic layers were dried over Na$_2$SO$_4$ and concentrated under reduced pressure. The resulting colorless oil was washed with petroleum ether and the precipitate formed was filtered off and dried under reduced pressure to afford tert-butyl 4-(bromomethyl)benzylcarbamate (1.1 g, 73%) as a white solid. $^1$H NMR (250 MHz, DMSO-d6) δ 7.38 (d, J=7.5 Hz, 2H), 7.21 (d, J=8.0 Hz, 2H), 4.68 (s, 2H), 4.10 (d, J=6.1 Hz, 2H), 1.39 (s, 9H). $^{13}$C NMR (63 MHz, DMSO-d6) δ 155.81, 140.51, 136.39, 129.27 (×2), 127.20 (×2), 77.86, 43.09, 34.55, 28.26 (×3).

4-(aminomethyl)benzyl alcohol (768 mg, 5.6 mmol) was dissolved in a mixture of H$_2$O (8.5 mL) and HBr (46% aqueous solution, 13 mL). The resulting mixture was refluxed for 3.5 hours, then the solvent was removed under reduced pressure, and the solid obtained was washed with Et$_2$O to afford (4-(bromomethyl)phenyl)methanamine hydrobromic salt as a grey powder (1 g, 89%). $^1$H NMR (250 MHz, DMSO-d6) δ 8.26 (brs, 2H), 7.48 (s, 4H), 4.71 (d, J=3.6 Hz, 2H), 4.03 (s, 2H). $^{13}$C NMR (63 MHz, DMSO-d6) δ 138.47, 134.07, 129.57 (×2), 129.37 (×2), 41.90, 34.03.

4-(aminomethyl)benzyl alcohol

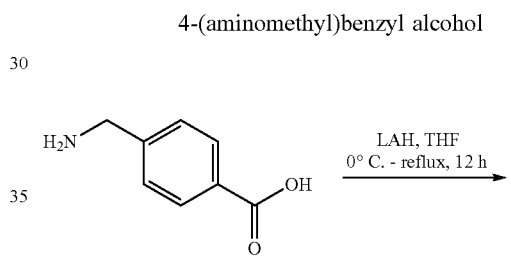

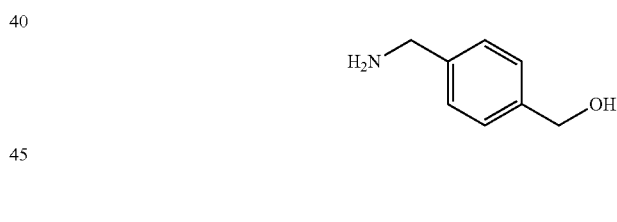

To a stirred suspension of 4-(aminomethyl)benzoic acid (10 g, 66.2 mmol) in tetrahydrofurane (100 mL) lithium aluminium hydride (10 g, 264.8 mmol) was added portionwise at 0° C. The mixture was heated to reflux and stirred overnight before cooling down again to 0° C. 10 mL of H$_2$O were added, then 15 mL of 10% NaOH and 30 mL of H$_2$O. The mixture was kept at 0° C. for 1 hour. Then the mixture was filtered through a pad of Celite and washed with EtOAc. The filtrate was concentrated to afford 4-(aminomethyl)benzyl alcohol as a yellow oil that crystallized to a beige solid after several minutes. The solid obtained was washed with Et$_2$O to afford 4-(aminomethyl)benzyl alcohol (8.8 g, yield 97%) as a light-beige powder. $^1$H NMR (250 MHz, CD$_3$OD) δ 7.32 (s, 4H), 4.58 (s, 2H), 3.78 (s, 2H). $^{13}$C NMR (63 MHz, CD$_3$OD) δ 142.21, 141.50, 128.53 (×2), 128.26 (×2), 64.96, 46.32.

Example 4: N-(4-((7-ethyl-2,6-dioxo-1H-purin-3(2H,6H,7H)-yl)methyl)benzyl)-1-propyl-1H-pyrazole-4-carboxamide (33c)

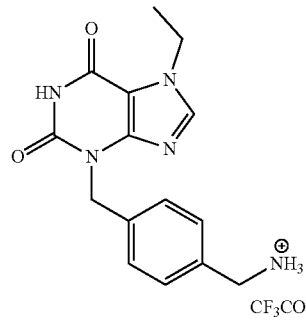

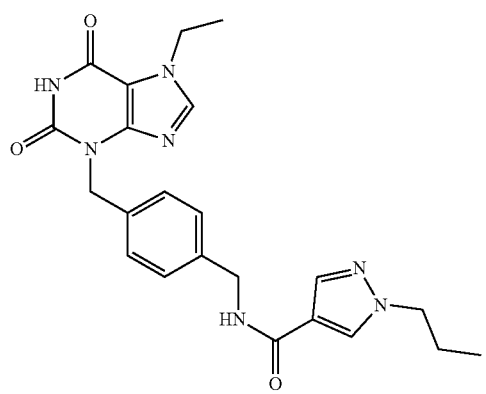

To 1-propyl-1H-pyrazole-4-carboxylic acid (3.73 mg, 0.024 mmol) was injected a solution of 20a (10 mg, 0.024 mmol) and triethylamine (7 µl, 0.048 mmol) in dimetylformamide (0.5 mL). A solution of BOP reagent (11 mg, 0.024 mmol) in dimethylformamide (0.5 mL) was added, and the resulting mixture was stirred at room temperature for 10 min, then dimethylformamide was removed under reduced pressure. The residue was suspended in H$_2$O (2 mL) and the precipitate collected by filtration to afford N-(4-((7-ethyl-2,6-dioxo-1H-purin-3(2H,6H,7H)-yl)methyl)benzyl)-1-propyl-1H-pyrazole-4-carboxamide 33c (6.6 mg, 63%) as a light-beige powder. $^1$H NMR (250 MHz, CD$_3$OD) δ 7.92 (s, 1H), 7.82 (s, 1H), 7.66 (s, 1H), 7.36 (d, J=9.7 Hz, 2H), 7.24 (d, J=8.1 Hz, 2H), 5.16 (s, 2H), 4.45 (s, 2H), 4.24-4.23 (m, 2H), 4.06 (d, J=7.0 Hz, 2H), 1.82 (dt, J=14.4, 7.2 Hz, 2H), 1.47 (t, J=7.2 Hz, 3H), 0.86 (t, J=7.4 Hz, 3H). LCMS C$_{22}$H$_{25}$N$_7$O$_3$ Rt=5.402 min, m/z=435.7, purity 99%.

Example 5: 3-((4-(aminomethyl)naphthalen-1-yl)methyl)-7-ethyl-1H-purine-2,6(3H,7H)-dione

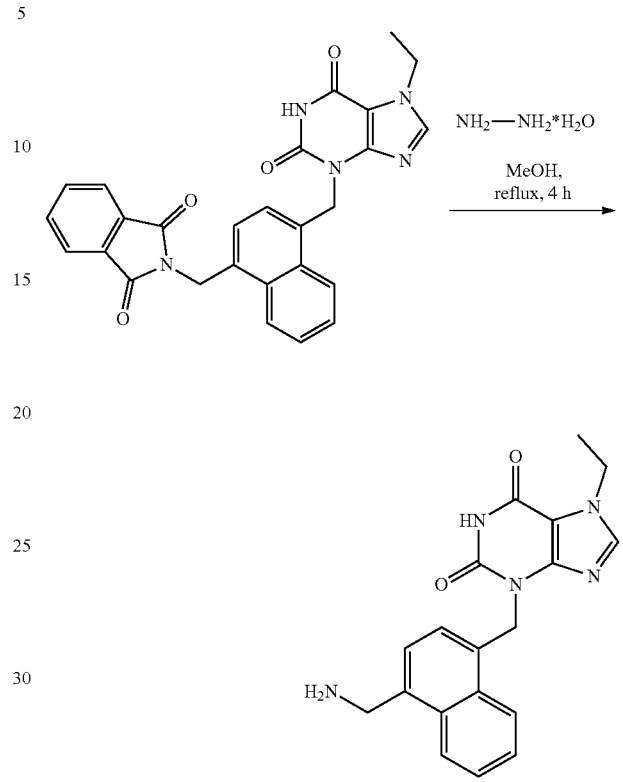

Hydrazine hydrate (141.5 µL, 2.94 mmol) was added to a suspension of 3-((4-((1,3-dioxoisoindolin-2-yl)methyl)naphthalen-1-yl)methyl)-7-ethyl-1H-purine-2,6(3H,7H)-dione (200 mg, 0.42 mmol) in methanol (7 mL) and the resulting mixture was stirred at reflux for 4 hours. The solvent was removed under reduced pressure, and the mixture was purified by column chromatography (eluent 15:1 CH$_2$Cl$_2$:MeOH+NH$_3$) to afford 3-((4-(aminomethyl)naphthalen-1-yl)methyl)-7-ethyl-1H-purine-2,6(3H,7H)-dione as a white solid (90 mg, yield 62%). $^1$H NMR (250 MHz, DMSO-d6) δ 8.27 (d, J=5.7 Hz, 1H), 8.18 (d, J=5.7 Hz, 1H), 8.01 (s, 1H), 7.67-7.54 (m, 2H), 7.42 (d, J=7.4 Hz, 1H), 7.04 (d, J=7.4 Hz, 1H), 5.57 (s, 2H), 4.25 (dd, J=13.8, 6.8 Hz, 2H), 4.16 (s, 2H), 1.40 (t, J=7.1 Hz, 3H). $^{13}$C NMR (63 MHz, DMSO-d6) δ 154.80, 151.00, 149.97, 142.02, 131.10, 130.60 (×2), 125.98, 125.89, 124.40 (×2), 123.89, 123.65, 122.84, 106.67, 54.97, 42.99, 41.63, 16.29.

3-((4-((1,3-dioxoisoindolin-2-yl)methyl)naphthalen-1-yl)methyl)-7-ethyl-1H-purine-2,6(3H,7H)-dione

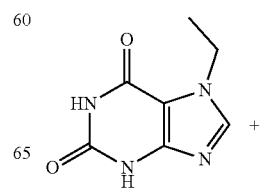

-continued

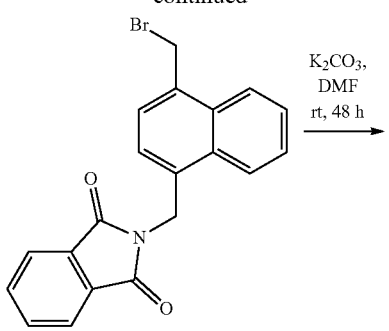

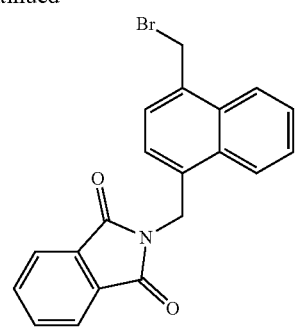

To a suspension of 2-(naphthalen-1-ylmethyl)isoindoline-1,3-dione (1.5 g, 5.2 mmol) and $(CH_2O)_n$ (235 mg, 7.8 mmol) in acetic acid (5 mL) HBr (1.1 mL) was added dropwise and the resulting mixture was stirred at 120° C. for 2 days. $H_2O$ (5 mL) was added, and the mixture was extracted with dichloromethane (5 mL×3), combined organic layers were collected, dried over $Na_2SO_4$ and the solvent was evaporated under reduced pressure to form a light-beige foam. The foam was dissolved in a mixture of dichloromethane and petroleum spirit to afford 2-((4-(bromomethyl)naphthalen-1-yl)methyl)isoindoline-1,3-dione as a beige precipitate (1.3 g, yield 66%) that was directly used in the next step without further purification.

2-(Naphthalen-1-ylmethyl)isoindoline-1,3-dione

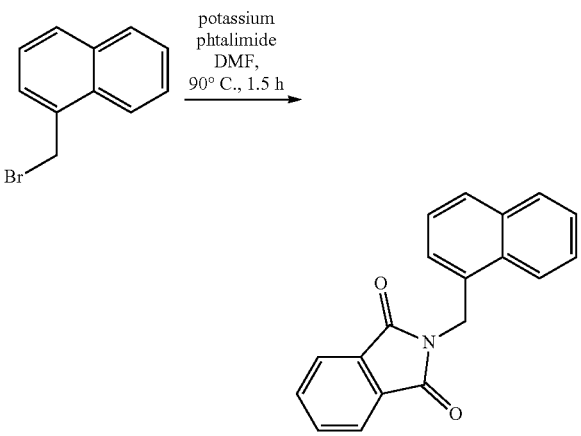

A suspension of 7-ethyl-1H-purine-2,6(3H,7H)-dione (321.2 mg, 1.78 mmol), 2-((4-(bromomethyl)naphthalen-1-yl)methyl)isoindoline-1,3-dione (1.3 g, 1.78 mmol) and potassium carbonate (246.2 mg, 1.78 mmol) in dimethylformamide (5 mL) was stirred at room temperature for 2 days. The solvent was removed under reduced pressure, $H_2O$ (5 mL) was added and a beige precipitate was filtered off, washed with $H_2O$ and dried under reduced pressure. The crude product was then purified by column chromatography (eluent $CH_2Cl_2$, then 10:1 $CH_2Cl_2$:MeOH) to achieve 3-((4-((1,3-dioxoisoindolin-2-yl)methyl)naphthalen-1-yl)methyl)-7-ethyl-1H-purine-2,6(3H,7H)-dione as a beige solid (490 mg, yield 57%). $^1$H NMR (250 MHz, $CDCl_3$) δ 7.65 (dddd, J=31.0, 15.0, 6.6, 4.1 Hz, 11H), 5.72 (s, 2H), 5.28 (s, 2H), 4.30 (q, J=7.2 Hz, 2H), 1.51 (t, J=7.2 Hz, 3H). $^{13}$C NMR (63 MHz, $CDCl_3$) δ 168.30 (×2), 154.45, 150.95, 150.86, 140.97, 134.18 (×2), 132.12 (×2), 131.70, 131.55, 131.51, 131.41, 126.65, 126.57, 126.42, 124.32, 124.10, 124.01, 123.48 (×2), 107.43, 43.80, 42.63, 39.57, 16.50.

2-((4-(Bromomethyl)naphthalen-1-yl)methyl)isoindoline-1,3-dione

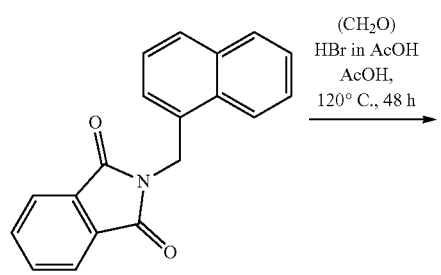

Potassium phtalimide (2.55 g, 14 mmol) was suspended in dimethylformamide (30 mL), and the reaction mixture was heated to 90° C. A solution of 1-(bromomethyl)naphthalene (3 g, 14 mmol) in dimethylformamide (20 mL) was added, and the resulting mixture was stirred at 90° C. for 1.5 hours. The solvent was removed under reduced pressure, $H_2O$ (10 mL) was added, and a white precipitate formed was filtered off, washed with $H_2O$ and $Et_2O$ and dried to afford 2-(naphthalen-1-ylmethyl)isoindoline-1,3-dione as a white powder (3 g, yield 76%). $^1$H NMR (250 MHz, $CDCl_3$) δ 8.37 (d, J=8.3 Hz, 1H), 7.90-7.39 (m, 10H), 5.34 (s, 2H). $^{13}$C NMR (63 MHz, $CDCl_3$) δ 168.39 (×2), 134.18 (×2), 133.89, 132.18 (×2), 131.47, 131.30, 128.86, 128.80, 127.43, 126.66, 125.96, 125.41, 123.60, 123.52 (×2), 39.65.

31

1-(Bromomethyl)naphthalene

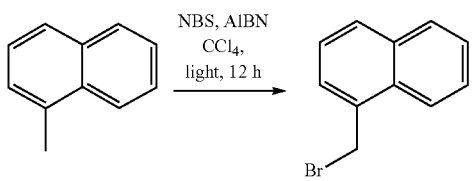

The suspension of 1-methylnaphtalene (3 g, 21 mmol), NBS (3.76 g, 1 eq) and AIBN (0.35 g, 0.1 eq) in 50 mL of CCl$_4$ was stirred under light overnight. CCl$_4$ was removed under reduced pressure and the crude mixture was purified by column chromatography (eluent petroleum ether) to achieve 1-(bromomethyl)naphthalene (3 g, yield 64%) as a colorless oil. $^1$H NMR (250 MHz, CDCl$_3$) δ 8.17 (d, J=8.5 Hz, 1H), 7.93-7.81 (m, 2H), 7.68-7.48 (m, 3H), 7.45-7.37 (m, 1H), 4.98 (s, 2H). $^{13}$C NMR (63 MHz, CDCl$_3$) δ 134.15, 133.38, 131.18, 129.95, 129.00, 127.90, 126.75, 126.38, 125.53, 123.86, 31.89.

Example 6: 3-(4-(aminomethyl)-2,5-dimethoxybenzyl)-7-ethyl-1H-purine-2,6(3H,7H)-dione

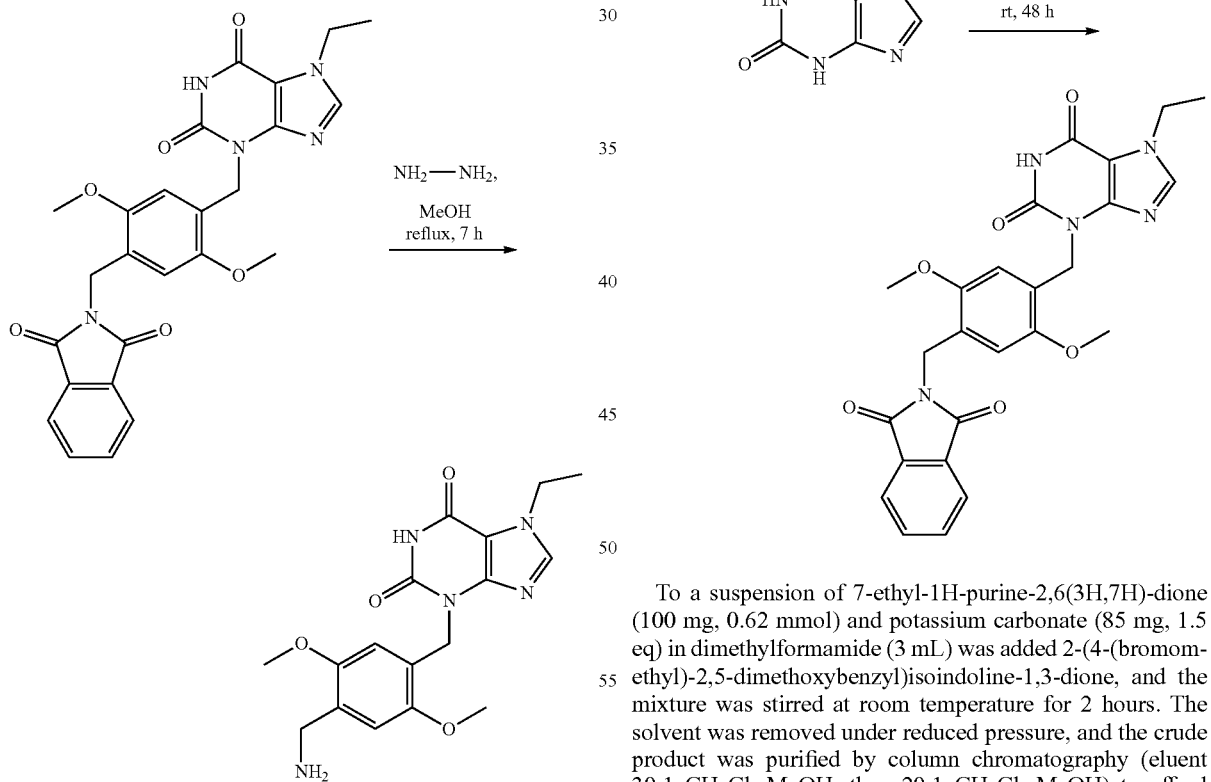

To a suspension of 3-(4-((1,3-dioxoisoindolin-2-yl)methyl)-2,5-dimethoxybenzyl)-7-ethyl-1H-purine-2,6(3H,7H)-dione (100 mg, 0.2 mmol) in methanol (10 mL) was added hydrazine (69.3 μL, 1.43 mmol), and the resulting mixture was stirred at reflux for 7 hours. The solvent was removed, the residue was dissolved in dichloromethane and washed with 1N HCl to afford 3-(4-(aminomethyl)-2,5-dimethoxybenzyl)-7-ethyl-1H-purine-2,6(3H,7H)-dione as a white powder (50 mg, yield 67%). $^1$H NMR (250 MHz, CDCl$_3$) δ 7.55 (s, 1H), 6.80 (s, 1H), 6.65 (s, 1H), 5.26 (s, 2H), 4.31 (q, J=7.2 Hz, 2H), 3.82-3.80 (m, 5H), 3.68 (s, 3H), 1.52 (t, J=7.2 Hz, 3H). $^{13}$C NMR (63 MHz, CDCl$_3$) δ 155.08, 151.39, 151.31, 151.10, 150.88, 140.89, 123.46 (×2), 112.21, 110.83, 107.31, 65.91, 56.36, 55.93, 42.49, 41.36, 16.45.

3-(4-((1,3-dioxoisoindolin-2-yl)methyl)-2,5-dimethoxybenzyl)-7-ethyl-1H-purine-2,6(3H,7H)-dione To a suspension of 7-ethyl-1H-purine-2,6(3H,7H)-dione (100 mg, 0.62 mmol) and potassium carbonate (85 mg, 1.5 eq) in dimethylformamide (3 mL) was added 2-(4-(bromomethyl)-2,5-dimethoxybenzyl)isoindoline-1,3-dione, and the mixture was stirred at room temperature for 2 hours. The solvent was removed under reduced pressure, and the crude product was purified by column chromatography (eluent 30:1 CH$_2$Cl$_2$:MeOH, then 20:1 CH$_2$Cl$_2$:MeOH) to afford 3-(4-((1,3-dioxoisoindolin-2-yl)methyl)-2,5-dimethoxybenzyl)-7-ethyl-1H-purine-2,6(3H,7H)-dione as a white powder (176 mg, yield 58%). $^1$H NMR (250 MHz, CDCl$_3$) δ 7.85-7.80 (m, 2H), 7.71-7.67 (m, 2H), 7.53 (s, 1H), 6.82 (s, 1H), 6.62 (s, 1H), 5.21 (s, 2H), 4.83 (s, 2H), 4.29 (q, J=7.2 Hz, 2H), 3.74 (s, 3H), 3.68 (s, 3H), 1.50 (t, J=7.2 Hz, 3H). $^{13}$C NMR (63 MHz, DMSO-d6) δ 167.79 (×2), 154.80, 150.99, 150.53, 150.38, 149.89, 141.95, 134.48 (×2), 131.74

(×2), 124.79, 123.79, 123.18 (×2), 111.69, 110.20, 106.53, 56.24, 56.21, 41.56, 41.07, 40.71, 16.27.

2-(4-(Bromomethyl)-2,5-dimethoxybenzyl)isoindoline-1,3-dione

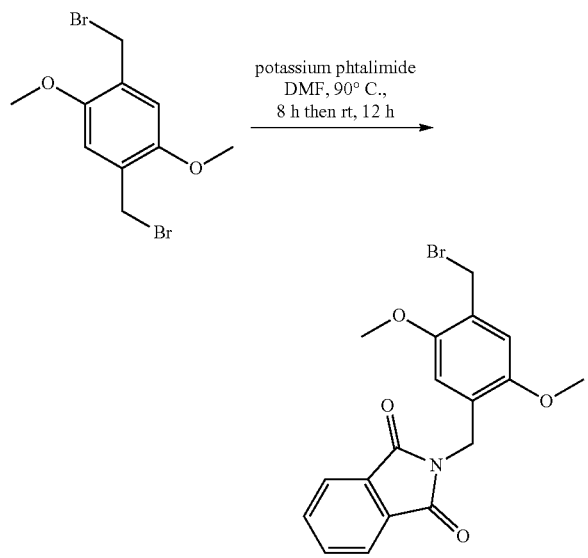

A suspension of potassium phtalimide (572 mg, 3.1 mmol) in dimethylformamide (5 mL) was heated to 90° C., then a suspension of 1,4-bis(bromomethyl)-2,5-dimethoxybenzene (1 g, 3.1 mmol) in dimethylformamide (5 mL) was added. The resulting mixture was stirred at 90° C. for 8 hours and then at room temperature overnight. The solvent was removed under reduced pressure and the crude product was purified by column chromatography (eluent 3:1 PE:EtOAc) to afford 2-(4-(bromomethyl)-2,5-dimethoxybenzyl) isoindoline-1,3-dione as a light-beige solid (423 mg, yield 35%). $^1$H NMR (250 MHz, CDCl$_3$) δ 7.86 (dd, J=5.5, 3.1 Hz, 2H), 7.72 (dd, J=5.4, 3.1 Hz, 2H), 6.84 (d, J=3.3 Hz, 2H), 4.87 (s, 2H), 4.52 (s, 2H), 3.82 (s, 3H), 3.80 (s, 3H). $^{13}$C NMR (63 MHz, CDCl$_3$) δ 168.15 (×2), 151.37, 151.16, 134.10 (×2), 132.15 (×2), 126.07, 125.99, 123.42 (×2), 113.49, 113.10, 56.42, 56.30, 36.89, 28.98.

1,4-Bis(bromomethyl)-2,5-dimethoxybenzene

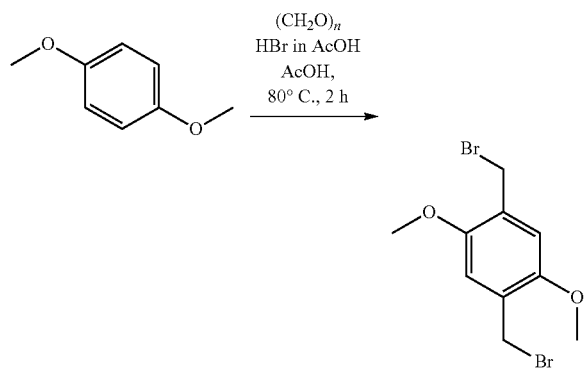

To a suspension of 1,4-dimethoxybenzene (4.1 g, 30 mmol) and (CH$_2$O)$_n$ (2 g, 66 mmol) in acetic acid (100 mL) HBr (33% solution in AcOH, 27 mL) was added dropwise, and the resulting mixture was stirred at 80° C. for 2 hours. The white precipitate formed was filtered off, washed with cold H$_2$O and dried to afford 1,4-bis(bromomethyl)-2,5-dimethoxybenzene (6.3 g, yield 66%) as a white solid. $^1$H NMR (250 MHz, CDCl$_3$) δ 6.87 (s, 2H), 4.54 (s, 4H), 3.87 (s, 6H). $^{13}$C NMR (63 MHz, CDCl$_3$) δ 151.38 (×2), 127.52 (×2), 113.93 (×2), 56.37 (×2), 28.75 (×2).

Example 7: N-(4-((8-((((6-butyl-5,7-dimethyl-[1,2,4]triazolo[1,5-a]pyrimidin-2-yl)thio)methyl)-7-ethyl-2,6-dioxo-1,2,6,7-tetrahydro-3H-purin-3-yl)methyl)benzyl)-2-oxo-2,3,4,5-tetrahydro-1H-benzo[b]azepine-7-sulfonamide (32c)

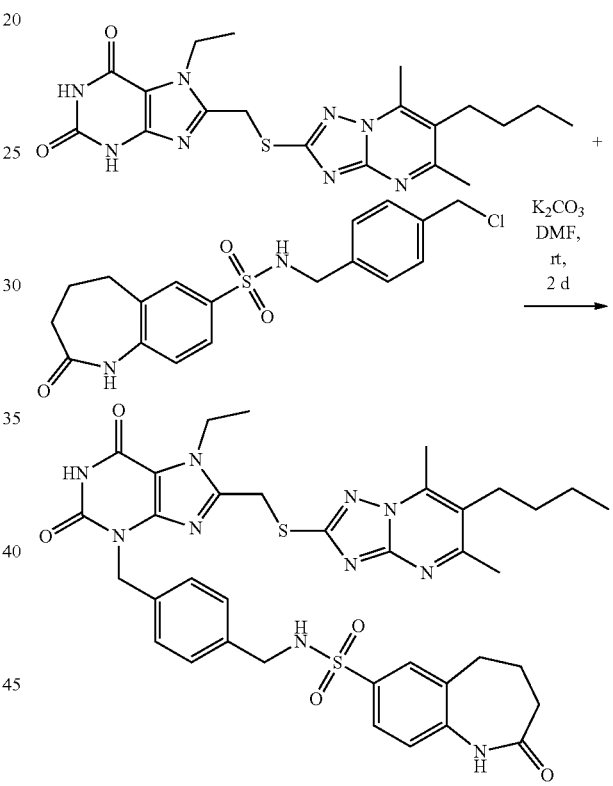

A suspension of 8-(((6-butyl-5,7-dimethyl--[1,2,4]triazolo[1,5-a]pyrimidin-2-yl)thio)methyl)-7-ethyl-3,7-dihydro-1H-purine-2,6-dione (10 mg, 0.023 mmol), N-(4-(chloromethyl)benzyl)-2-oxo-2,3,4,5-tetrahydro-1H-benzo[b]azepine-7-sulfonamide (8.84 mg, 0.023 mmol) and potassium carbonate (9.7 mg, 0.069 mmol) in dimethylformamide (1 mL) was stirred at room temperature for 2 days. The solvent was removed under reduced pressure, and the crude product was purified by column chromatography (eluent 10:1 CH$_2$Cl$_2$:MeOH) to afford N-(4-((8-(((6-butyl-5,7-dimethyl-[1,2,4]triazolo[1,5-a]pyrimidin-2-yl)thio)methyl)-7-ethyl-2,6-dioxo-1,2,6,7-tetrahydro-3H-purin-3-yl)methyl)benzyl)-2-oxo-2,3,4,5-tetrahydro-1H-benzo[b]azepine-7-sulfonamide 32c (8 mg, 45%) as a beige solid. $^1$H NMR (250 MHz, CD$_3$OD+CDCl$_3$) δ 7.56-7.48 (m, 1H), 7.21 (d, J=8.1 Hz, 2H), 7.10-6.90 (m, 4H), 5.08 (s, 2H), 4.68 (s, 2H), 4.49 (d, J=7.0 Hz, 2H), 4.04 (s, 2H), 2.75 (s, 6H), 2.66 (s, 3H), 2.26 (t, J=8.3 Hz, 5H), 1.45 (t, J=7.1 Hz, 7H), 0.98 (t, J=6.9 Hz, 3H). $^{13}$C NMR (63 MHz, CD$_3$OD) δ 176.57, 176.48, 165.50, 164.19, 155.79, 154.42, 152.09, 150.17, 145.00, 142.77, 138.00, 137.19, 136.29, 135.60, 129.22, 128.89 (×2), 128.62 (×2), 127.06, 123.07, 122.69, 108.52, 47.23, 45.94, 41.95, 33.52, 32.37, 30.99, 29.09, 28.39, 26.80, 23.73, 23.45, 16.75, 14.31, 14.09. LCMS C$_{37}$H$_{42}$N$_{10}$O$_5$S$_2$ Rt=6.450, m/z=770.4, purity >95%.

N-(4-(chloromethyl)benzyl)-2-oxo-2,3,4,5-tetrahydro-1H-benzo[b]azepine-7-sulfonamide

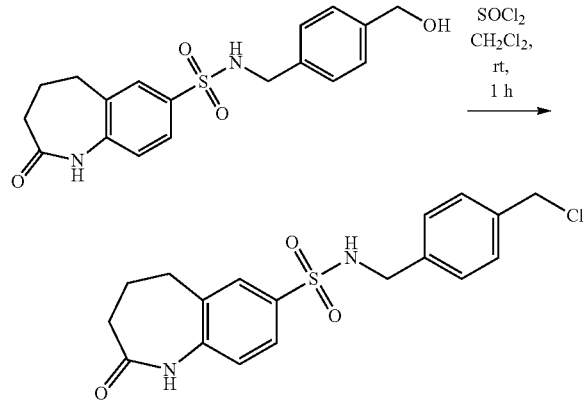

Thionyl chloride (156 µL, 2.15 mmol) was added to a solution of N-(4-(hydroxymethyl)benzyl)-2-oxo-2,3,4,5-tetrahydro-1H-benzo[b]azepine-7-sulfonamide (155 mg, 0.43 mmol) in dichloromethane (2 mL). A resulting mixture was stirred at room temperature for 1 hour. The solvent was evaporated to afford N-(4-(chloromethyl)benzyl)-2-oxo-2,3,4,5-tetrahydro-1H-benzo[b]azepine-7-sulfonamide (163 mg, 100%) as a white solid, that was directly use in the next step without purification. $^1$H NMR (250 MHz, CD$_3$OD) δ 7.65 (d, J=8.1 Hz, 2H), 7.22 (dd, J=21.0, 8.0 Hz, 4H), 7.06 (d, J=8.0 Hz, 1H), 4.56 (s, 2H), 4.12 (s, 2H), 2.78 (t, J=6.8 Hz, 2H), 2.25 (dd, J=11.0, 5.7 Hz, 4H).

N-(4-(hydroxymethyl)benzyl)-2-oxo-2,3,4,5-tetrahydro-1H-benzo[b]azepine-7-sulfonamide

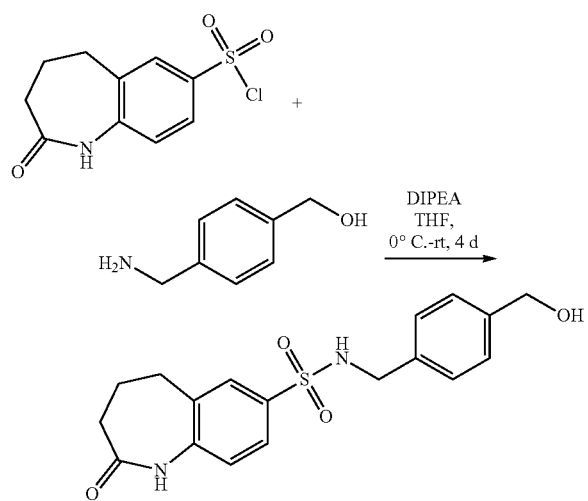

Under argon to a solution of (4-(aminomethyl)phenyl)methanol (100 mg, 0.73 mmol) and DIPEA (254 µL, 1.46 mmol) in tetrahydrofurane (6 mL) at 0° C. 1b (189 mg, 0.73 mmol) was added dropwise as a solution in tetrahydrofurane (4 mL). After stirring for 30 min at 0° C., the mixture was allowed to warm to room temperature and stirred for 4 days. A white precipitate formed was filtered through Celite, the filtrate was evaporated under reduced pressure to afford viscous yellow oil. Dichloromethane (1 mL) was added and a precipitate formed was filtered, washed with a small amount of dichloromethane and diethyl ether and dried under reduced pressure to afford N-(4-(hydroxymethyl)benzyl)-2-oxo-2,3,4,5-tetrahydro-1H-benzo[b]azepine-7-sulfonamide (155 mg, 59%) as a white solid. $^1$H NMR (250 MHz, CD$_3$OD) δ 7.71-7.62 (m, 2H), 7.19 (q, J=8.2 Hz, 4H), 7.08 (d, J=8.1 Hz, 1H), 4.53 (s, 2H), 4.10 (s, 2H), 2.79 (t, J=6.7 Hz, 2H), 2.34-2.17 (m, 4H). $^{13}$C NMR (63 MHz, CD$_3$OD) δ 177.08, 143.49, 141.95, 138.82, 137.58, 136.23, 129.71, 128.96 (×2), 127.93 (×2), 127.50, 123.05, 64.77, 47.65, 33.87, 31.30, 29.53.

8-(((6-butyl-5,7-dimethyl-[1,2,4]triazolo[1,5-a]pyrimidin-2-yl)thio)methyl)-7-ethyl-3,7-dihydro-1H-purine-2,6-dione

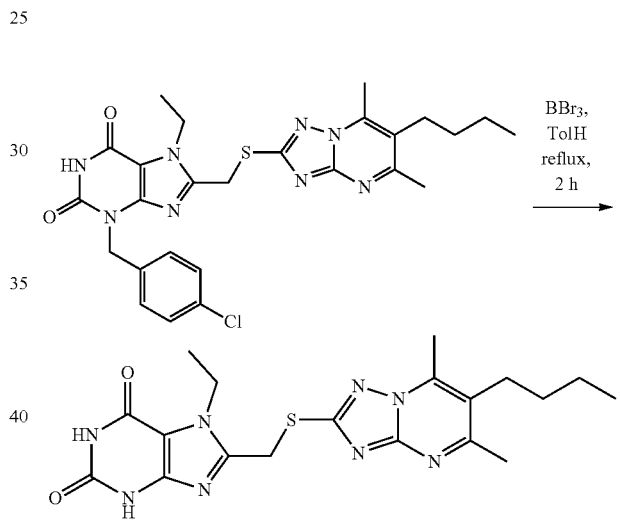

To a suspension of 8-(((6-butyl-5,7-dimethyl-[1,2,4]triazolo[1,5-a]pyrimidin-2-yl)thio)methyl)-3-(4-chlorobenzyl)-7-ethyl-3,7-dihydro-1H-purine-2,6-dione (115 mg, 0.21 mmol) in toluene (5 mL) 1M solution of boron tribromide in dichloromethane (2.1 mL, 2.1 mmol) was injected dropwise. The resulting mixture was stirred at reflux for 2 hours. The solvent was removed, the residue was dissolved in methanol (7 mL), concentrated hydrochloric acid (1 mL) was injected followed by stirring at room temperature for 2 hours. Methanol was removed under reduced pressure and the residue was extracted with dichloromethane (5 mL). An aqueous layer was collected and dried under vacuum to give a product as a light orange solid (90 mg, 100%). $^1$H NMR (250 MHz, CD$_3$OD+CDCl$_3$) δ 4.74 (s, 2H), 4.54 (d, J=7.3 Hz, 2H), 2.79 (s, 5H), 2.69 (s, 3H), 1.57-1.42 (m, 7H), 0.99 (t, J=6.3 Hz, 3H). $^{13}$C NMR (63 MHz, CD$_3$OD) δ 169.17, 161.18, 156.58, 151.08, 148.68, 148.11, 147.42, 126.44, 108.56, 42.88, 32.23, 28.66, 26.78, 23.78, 23.72, 16.43, 14.41, 14.10.

By implementing the syntheses as described above, the compounds as disclosed in the below table have been prepared.

TABLE 1
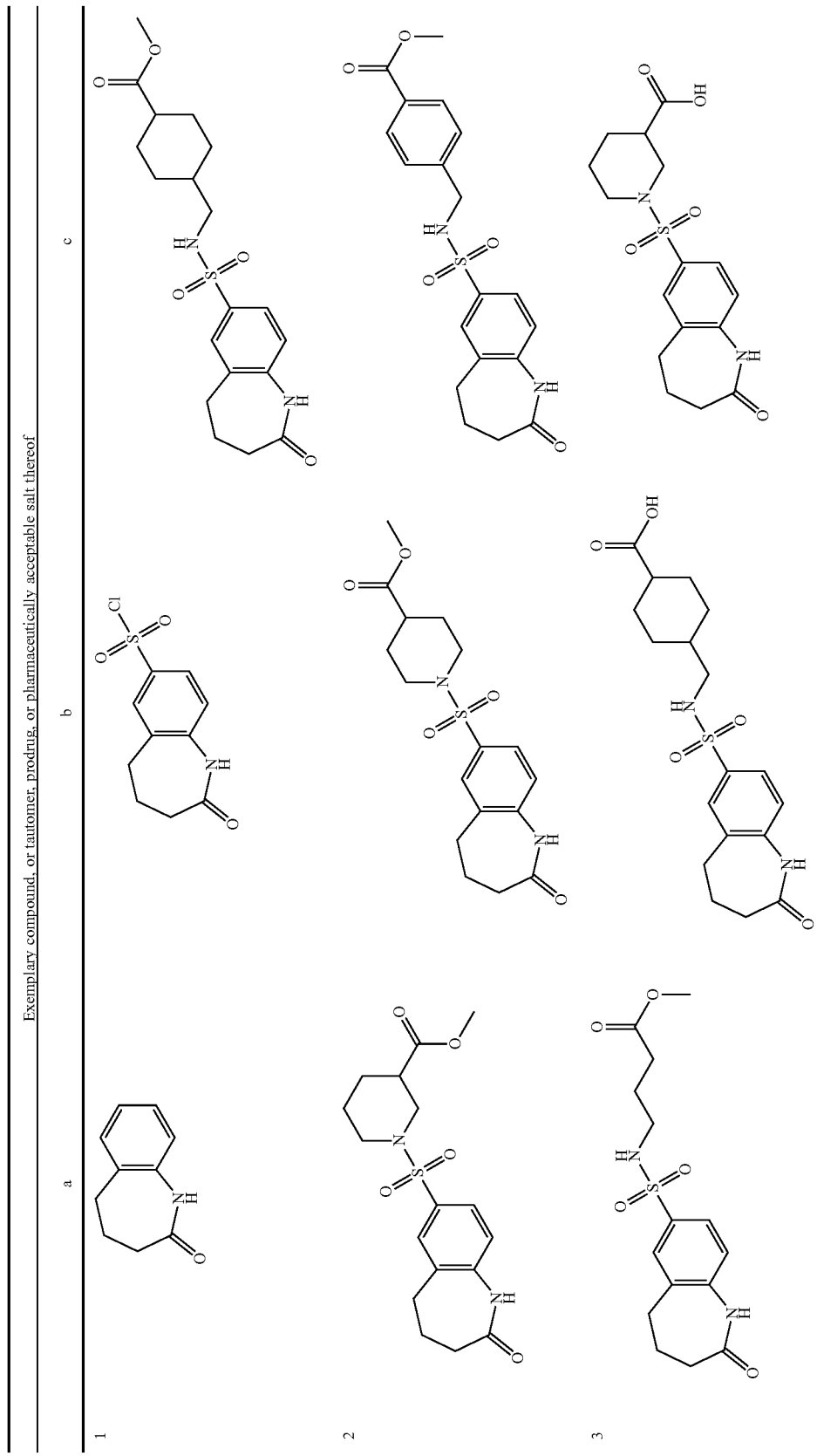

TABLE 1-continued

Exemplary compound, or tautomer, prodrug, or pharmaceutically acceptable salt thereof

| | a | b | c |
|---|---|---|---|
| 4 | | | |
| 5 | | | Cis-/trans-mixture |
| 6 | | | |

TABLE 1-continued

Exemplary compound, or tautomer, prodrug, or pharmaceutically acceptable salt thereof

| | a | b | c |
|---|---|---|---|
| 7 | | | |
| 8 | | s-/trans-mixture | |
| 9 | | | |
| 10 | | | |

TABLE 1-continued

Exemplary compound, or tautomer, prodrug, or pharmaceutically acceptable salt thereof

| | a | b | c |
|---|---|---|---|
| 11 | | | |
| 12 | | | |
| 13 | | | |
| 14 | | | |

TABLE 1-continued

Exemplary compound, or tautomer, prodrug, or pharmaceutically acceptable salt thereof

| | a | b | c |
|---|---|---|---|
| 15 | | | |
| 16 | | | |
| 17 | | | |
| 18 | | | |

TABLE 1-continued
Exemplary compound, or tautomer, prodrug, or pharmaceutically acceptable salt thereof
| | a | b | c |
|---|---|---|---|
| 19 | 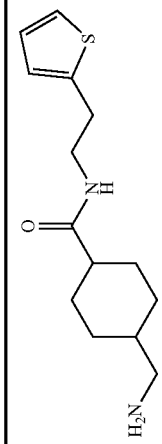 |  | 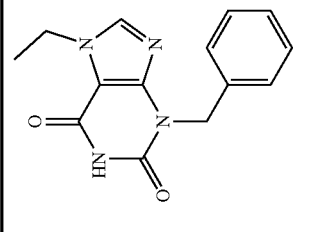 |
| 20 |  | 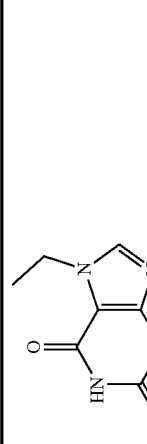 | 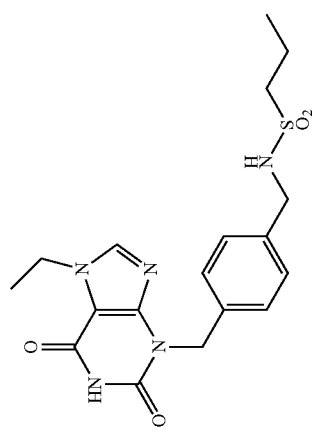 |
| 21 | 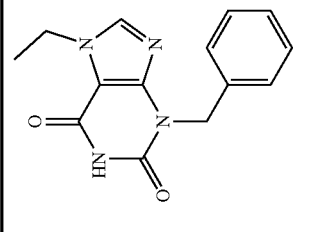 | 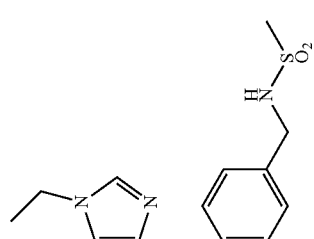 | 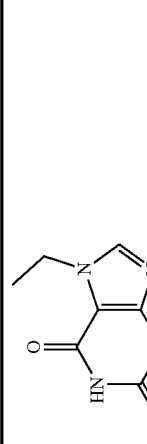 |

TABLE 1-continued

Exemplary compound, or tautomer, prodrug, or pharmaceutically acceptable salt thereof

| | a | b | c |
|---|---|---|---|
| 22 | | | |
| 23 | | | |
| 24 | | | |

TABLE 1-continued

Exemplary compound, or tautomer, prodrug, or pharmaceutically acceptable salt thereof

| | a | b | c |
|---|---|---|---|
| 25 | | | |
| 26 | | | |
| 27 | | | |

TABLE 1-continued

Exemplary compound, or tautomer, prodrug, or pharmaceutically acceptable salt thereof

| | a | b | c |
|---|---|---|---|
| 28 | | | |
| 29 | | | |
| 30 | | | |

TABLE 1-continued

Exemplary compound, or tautomer, prodrug, or pharmaceutically acceptable salt thereof

| | a | b | c |
|---|---|---|---|
| 31 | | | |
| 32 | | | |

TABLE 1-continued

Exemplary compound, or tautomer, prodrug, or pharmaceutically acceptable salt thereof

| | a | b | c |
|---|---|---|---|
| 33 | | | |
| 34 | | | |

TABLE 1-continued

Exemplary compound, or tautomer, prodrug, or pharmaceutically acceptable salt thereof

| | a | b | c |
|---|---|---|---|
| 35 | | | |
| 36 | | | |

TABLE 1-continued

Exemplary compound, or tautomer, prodrug, or pharmaceutically acceptable salt thereof

| | a | b | c |
|---|---|---|---|
| 37 | (structure) | (structure) | (structure) |
| 38 | (structure) | (structure) | (structure) |

TABLE 1-continued

Exemplary compound, or tautomer, prodrug, or pharmaceutically acceptable salt thereof

| | a | b | c |
|---|---|---|---|
| 39 | [structure] | [structure] | [structure] |
| 40 | [structure] | [structure] | [structure] |

TABLE 1-continued
Exemplary compound, or tautomer, prodrug, or pharmaceutically acceptable salt thereof
| | a | b | c |
|---|---|---|---|
| 41 | 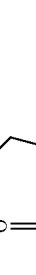 | 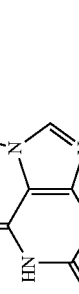 | 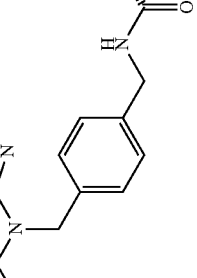 |
| 42 | 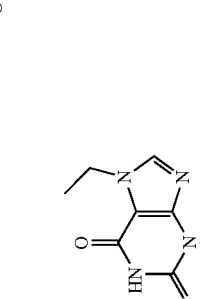 | 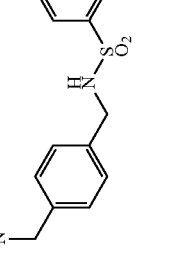 | 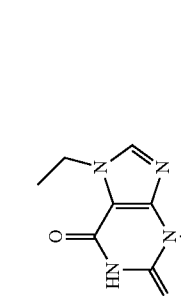 |
| 43 | 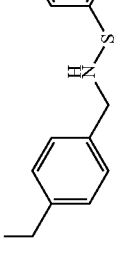 |  |  |

TABLE 1-continued

Exemplary compound, or tautomer, prodrug, or pharmaceutically acceptable salt thereof

| | a | b | c |
|---|---|---|---|
| 44 | (structure) | (structure) | (structure) |
| 45 | (structure) | | |

Activity of the Compounds According to the Invention

Example 1: HTRF Assay

HTRF assays were performed in white 384 Well Small Volume™ HiBase Polystyrene Microplates (Greiner) with a total working volume of 20 µL. Compounds were dispensed, with 100 nL per well (0.5% final DMSO), from a concentration stock of 10 mM in 100% DMSO and with serial DMSO dilutions, using an Echo® 550 robot from the Access Labcyte platform (Labcyte) and based on the transfer of liquid by acoustic wave. Then, 19.5 µL of buffer is added, using a Multidrop Combi (Thermo Fisher Scientific). Finally, for each assay, 200 nL of master mix (protein+donor+acceptor) and 200 nL of peptide Is added in the assay wells according to the final concentration and buffer described in Table 3, using the Echo® 550 robot (Labcyte). The $IC_{50}$ measurements were performed in triplicates (Table 2 and 3). All HTRF reagents (donor and acceptor) were purchased from CisBio Bioassays and reconstituted according to the supplier protocols. The peptide was purchased from Genic Bio Synthetic. The BRD4(1) protein was produced and purified in the laboratory. HTRF signals were measured, after a final incubation (3 h or 6 h or overnight at room temperature or 4° C., according to the bromodomain), using a PHERAstar FS (BMG Labtech) with an excitation filter at 337 nm and fluorescence wavelength measurement at 620 and 665 nm, an integration delay of 60 µs and an integration time of 500 µs. Results were analyzed with a two-wavelengths signal ratio: [intensity (665 nm)/intensity (620 nm)]*104.

Percentage of inhibition was calculated using the following equation: % inhibition=[(compound signal)−(min signal)]/[(max signal)−(min signal)]*100, where 'max signal' is the signal ratio with the compound vehicle alone (DMSO) and 'min signal' the signal ratio without peptide. For $IC_{50}$ measurements, values were normalized and fitted with Prism (GraphPad software) using the following equation: Y=100/(1+((X/IC50)^Hill slope)).

TABLE 2

Effect of various compounds of invention on BRD4(BD1) activity[a]

| Cmpd ($IC_{50}$ µM) | Cmpd ($IC_{50}$ µM) | Cmpd ($IC_{50}$ µM) | Cmpd ($IC_{50}$ µM) | Cmpd ($IC_{50}$ µM) | Cmpd ($IC_{50}$ µM) |
|---|---|---|---|---|---|
| 1a (NA) | 1b (NA) | 1c (53) | 2a (NA) | 2b (NA) | 2c (NA) |
| 3a (NA) | 3b (NA) | 3c (NA) | 4a (NA) | 4b (NA) | 4c (NA) |

TABLE 2-continued

Effect of various compounds of invention on BRD4(BD1) activity[a]

| Cmpd ($IC_{50}$ µM) | Cmpd ($IC_{50}$ µM) | Cmpd ($IC_{50}$ µM) | Cmpd ($IC_{50}$ µM) | Cmpd ($IC_{50}$ µM) | Cmpd ($IC_{50}$ µM) |
|---|---|---|---|---|---|
| 5a (>50) | 5b (3.8) | 5c (7.0) | 6a (29) | 6b (25) | 6c (30) |
| 7a (9.6) | 7b (19) | 7c (23) | 8a (22) | 8b (ND) | 8c (18) |
| 9a (16) | 9b (NA) | 9c (NA) | 10a (NA) | 10b (NA) | 10c (NA) |
| 11a (NA) | 11b (>50) | 11c (>50) | 12a (NA) | 12b (NA) | 12c (NA) |
| 13a (NA) | 13b (NA) | 13c (NA) | 14a (>25) | 14b (>25) | 14c (>25) |
| 15a (NA) | 15b (46) | 15c (7.8) | 16a (11) | 16b (NA) | 16c (NA) |
| 17a (NA) | 17b (NA) | 16c (NA) | 18a (NA) | 18b (NA) | 18c (ND) |
| 19a (ND) | 19b (12) | 19c (ND) | 20a (27) | 20b (4.3) | 20c (3.6) |
| 21a (2.9) | 21b (5.2) | 21c (1.4) | 22a (4.5) | 22b (7.5) | 22c (1.4) |
| 23a (3.5) | 23b (1.7) | 23c (1.3) | 24a (2.7) | 24b (0.846) | 24c (1.7) |
| 25a (0.284) | 25b (0.779) | 25c (1.6) | 26a (2.2) | 26b (0.769) | 26c (0.817) |
| 27a (1.3) | 27b (0.766) | 27c (0.283) | 28a (1.3) | 28b (0.729) | 28c (0.687) |
| 29a (1.6) | 29b (0.450) | 29c (0.814) | 30a (0.600) | 30b (0.687) | 30c (0.510) |
| 31a (0.355) | 31b (0.723) | 31c (3.5) | 32a (13) | 32b (0.964) | 32c (1.1) |
| 33a (0.371) | 33b (4.7) | 33c (4.5) | 34a (4.3) | 34b (2.8) | 34c (0.749) |
| 35a (2.8) | 35b (7.0) | 35c (1.8) | 36a (2.2) | 32b (2.7) | 36c (3.1) |
| 37a (2.0) | 37b (4.9) | 36c (0.229) | 38a (1.7) | 38b (8.1) | 38c (5.5) |
| 39a (6.8) | 39b (2.3) | 39c (1.5) | 40a (18) | 40b (32) | 40c (13) |
| 41a (>50) | 41b (>50) | 41c (>50) | 42a (>50) | 42b (32) | 42c (0.750) |
| 43a (0.202) | 43b (0.096) | 43c (0.074) | 44a (ND) | 44b (0.123) | 44c (0.522) |
| 45a (0.087) | | | | | |

[a]Drug concentration that inhibits protein-protein interaction by 50%.
ND abbreviation stands for Not Determined.
NA abbreviation stands for Not Applicable ($IC_{50}$ > maximal concentration of compound used).

Example 2: Brodomodomain "BET" Selectivity Profiles (HTRF Assay)

Selectivity profiles of bromodomain inhibitors were performed as described in HTRF screen section. Concentration of histone peptide was optimized to ensure sufficient signal to noise ratio, sufficient sensitivity for detection of weak inhibitors and comparable data from one bromodomain to another. HTRF detection reagents (EPIgeneous™ Binding Domain kits) were purchased from Cisbio Bioassays and used according to supplier's protocol. GST tagged bromodomain proteins were purchased from BPS Bioscience and histone peptide from Genic Bio Synthetic.

TABLE 3

Selectivity profiles of compounds of invention towards the BET

| | Bromodomain ($IC_{50}$ nM)[a] | | | | | | | | Ratio | | |
|---|---|---|---|---|---|---|---|---|---|---|---|
| Cmpd | Brd4(8D1) | Brd3(BD1) | Brd2(BD1) | Brdt(BD1) | Brd4(BD2) | Brd3(BD2) | Brd2(BD2) | ATAD2 | 4-1 vs 4-2 | 3-1 vs 3-2 | 2-1 vs 2-2 |
| 5b | 3827 | 2380 | 6347 | 14580 | NA | NA | NA | NA | >13 | >21 | >8 |
| 7a | 9553 | 22190 | 16150 | 9157 | 20840 | 47190 | 7106 | NA | 2 | 2 | 0.4 |
| 9a | 15700 | 5048 | 10350 | 9169 | NA | NA | 33940 | NA | >3 | >10 | 3 |
| 16a | 10870 | 8622 | 8703 | 12460 | NA | NA | NA | NA | >5 | >6 | >6 |
| 24b | 846 | 1004 | 3334 | 6257 | 5848 | 11982 | 6050 | NA | 7 | 12 | 2 |
| 25a | 284 | 507 | 2105 | 3471 | 4054 | 3168 | 3198 | NA | 14 | 6 | 2 |
| 25b | 779 | 1536 | 1384 | 7437 | 12802 | 12360 | 10486 | NA | 16 | 8 | 8 |
| 25c | 1595 | 4767 | 4177 | 14043 | 21185 | 17428 | 23514 | NA | 13 | 4 | 7 |
| 27b | 766 | 940 | 3488 | 2150 | 8314 | 3031 | 5577 | NA | 11 | 3 | 2 |

TABLE 3-continued

Selectivity profiles of compounds of invention towards the BET

| | Bromodomain (IC$_{50}$ nM)[a] | | | | | | | | Ratio | | |
| --- | --- | --- | --- | --- | --- | --- | --- | --- | --- | --- | --- |
| | | | | | | | | | 4-1 vs 4-2 | 3-1 vs 3-2 | 2-1 vs 2-2 |
| Cmpd | Brd4(BD1) | Brd3(BD1) | Brd2(BD1) | Brdt(BD1) | Brd4(BD2) | Brd3(BD2) | Brd2(BD2) | ATAD2 | | | |
| 27c | 283 | 456 | 336 | 356 | 2779 | 3473 | 1605 | NA | 10 | 8 | 5 |
| 29b | 450 | 897 | 3314 | 19659 | 17723 | 13538 | 15988 | 24647 | 39 | 15 | 5 |
| 29c | 814 | 1596 | 5470 | 7440 | 12165 | 18931 | 14698 | NA | 15 | 12 | 3 |
| 30c | 510 | 633 | 868 | 1179 | 4588 | 3157 | 2494 | NA | 9 | 5 | 3 |
| 31a | 355 | 596 | 1456 | 8508 | 9708 | 13462 | 12771 | NA | 27 | 23 | 9 |
| 31c | 3463 | 5711 | 4350 | 3357 | 4210 | 2133 | 3075 | NA | 1 | 0.4 | 0.7 |
| 32b | 984 | 9598 | 4372 | 9541 | 28001 | 7275 | 3937 | NA | 29 | 0.8 | 0.9 |
| 32c | 1079 | 4427 | 4674 | 18930 | 9151 | 4156 | 3357 | NA | 9 | 1 | 0.7 |
| 43a | 202 | 258 | 367 | 474 | 4392 | 2436 | 2264 | NA | 22 | 10 | >6 |
| 43b | 96 | 130 | 260 | 1100 | 3300 | 2900 | 2400 | NA | 34 | 22 | 9 |
| 43c | 74 | 132 | 183 | 352 | 2310 | 2167 | 1222 | NA | 31 | 16 | 7 |
| 44b | 123 | 230 | 352 | 397 | 4241 | 3325 | 1962 | NA | 34 | 14 | 6 |
| 45a | 87 | 161 | 321 | 432 | 2668 | 1636 | 1067 | NA | 31 | 10 | 3 |

[a]Drug concentration that inhibits protein-protein interaction by 50%. Data are the mean of three experiments.
NA abbreviation stands for Not Applicable (IC$_{50}$ > maximal concentration of compound used (50 μM)).
[b]ATAD2 is used as a non-BET family member bromodomain control.

TABLE 4

HTRF selectivity experimental procedures[a]

| Protein name | MIX 1 | | | | | MIX 2 | | Assay | |
| --- | --- | --- | --- | --- | --- | --- | --- | --- | --- |
| | (nM) | Peptide name | (nM) | Donor name | (nM) | Acceptor name | (nM) | buffer[b] | DMSO |
| GST-BRD4(BD1) | 5 | H4 KAc 5/8/12/16 peptide | 15 | MAb Anti GST-Keu | 0.5 | Streptavidin d2 | 1.875 | Buffer A | 0.5% |
| GST-BRD3(BD1) | 5 | H4 KAc 5/8/12/16 peptide | 15 | MAb Anti GST-Keu | 0.5 | Streptavidin d2 | 1.875 | Buffer A | 0.5% |
| GST-BRD2(BD1) | 5 | H4 KAc 5/8/12/16 peptide | 15 | MAb Anti GST-Keu | 0.5 | Streptavidin d2 | 1.875 | Buffer A | 0.5% |
| GST-BRDT(BD1) | 5 | H4 KAc 5/8/12/16 peptide | 150 | MAb Anti GST-Keu | 0.5 | Streptavidin XL665 | 18.75 | Buffer A | 0.5% |
| GST-BRD4(BD2) | 5 | H4 KAc 5/8/12/16 peptide | 150 | MAb Anti GST-Keu | 0.5 | Streptavidin XL665 | 18.75 | Buffer A | 0.5% |
| GST-BRD3(BD2) | 5 | H4 KAc 5/8/12/16 peptide | 150 | MAb Anti GST-Keu | 0.5 | Streptavidin XL665 | 18.75 | Buffer A | 0.5% |
| GST-BRD2(BD2) | 5 | H4 KAc 5/8/12/16 peptide | 150 | MAb Anti GST-Keu | 0.5 | Streptavidin XL665 | 18.75 | Buffer A | 0.5% |
| GST-ATAD2 | 5 | H4 KAc 5/8/12/16 peptide | 150 | MAb Anti GST-KTb | 0.5 | Streptavidin XL665 | 18.75 | Buffer B | 0.5% |

[a]For each bromodomain, concentrations of protein, peptide, donor and acceptor have been optimized and are presented in this summary table also indicating the donor and acceptor type as well as the final DMSO concentration and buffer composition.
[b]Buffer A: 50 mM Hepes, pH7.5, 400 mM KF, BSA 0.1%.

Example 3: Brodomodomain Selectivity Profiles Using the Thermal Shift Assays (TSA)

TSA "Bromoscan" assays (Reaction Biology) were performed in 384 well RT-PCR plate (BioRad) with a total working volume of 15 μL. The "BromoMelT™, containing the 61 GST- or His-tagged-bromodomains, SYPRO® Orange and a mix compounds as control, was purchased from Reaction Biology. For each point, 3 μL of protein (1×) and 12 μL master mix (buffer+SYPRO® Orange+compound at 25 μM or control mix compounds or DMSO (0.5%)) were mixed in plate. The plate was placed in a CFX384 RTQPC (BioRad), and heated 10 seconds at 25° C., then the temperature was increased from 25° C. to 90° C., by increment of 0.5° C. every 30 seconds. The fluorescence was recorded using FRET filters.

The compounds 27c is pan-BET selective, 30c is BRD4 (1) and BRD3(1) selective, 31a is not pan-BET selective.

Example 4: Isothermal Titration Calorimetry Assays

ITC was used to evaluate the thermodynamics parameters of the binding between BRD4 (BD1) and the selected compounds. Titrations were carried out on a MicroCal ITC200 microcalorimeter (GE Healthcare, Piscataway, N.J.). Each experiment was designed using a titrant concentration (protein in the syringe generally between 100 and 400 μM) set 10 to 15 times the analyte concentration (compound in the cell generally between 10 and 40 μM) and using 13 injections at 25° C. A first small injection (generally 0.2 μL) was included in the titration protocol in order to remove air bubbles trapped in the syringe prior titration. Raw data were scaled after setting the zero to the titration saturation heat value. Integrated raw ITC data were fitted to a one site non-linear least squares fit model using the MicroCal Origin plugin as implemented in Origin 7 (Origin Lab). Finally, ΔG and TΔS values were calculated from the fitted ΔH and $K_A$ values using the equations ΔG=−R.T.in$K_A$ and ΔG=ΔH−TΔS.

TABLE 5

Binding affinity (Kd) to BRD4(1) determined by Isothermal Titration Calorimetry

| Compound (Kd μM) | | | | | | |
|---|---|---|---|---|---|---|
| 5b | 5c | 7a | 7b | 9a | 15c | 16a |
| (2.2) | (2.8) | (3.5) | (8.8) | (3.4) | (2.2) | (5.8) |
| 27c | 29c | 30c | 31a | 32c | 33a | 43b |
| (0.129) | (1.1) | (0.641) | (0.433) | (2.1) | (20.5) | (0.11) |
| 43c | 44b | 45a | | | | |
| (0.090) | (0.170) | (0.060) | | | | |

Example 5: Cell-Based Assays

Cells and Cell Culture

The human leukemia cell line Jurkat (ATCC® TIB-152) and Molm14 was maintained in RPMI-1640 medium or MEMα, respectively and supplemented both with 10% FBS at 37° C. and 5% $CO_2$.

Cytotoxicity Experiments

In antiproliferative assays, compounds were assayed for their growth inhibiting activity towards the described cancer cell lines using the Cell Titer-Glo Luminescent Cell Viability Assay as described by the manufacturer (Promega Corporation). Briefly, 10.000 cells were plated onto 96 well-plates (white with clear bottom (3610, Corning Costar)) in 90 μL media per well immediately before assay. 10 μL of compounds were added at different concentrations (ranging from 50 μM to 6 nM) to each well and cell cultures were incubated 37° C. during 72 h. Vehicle (DMSO) was used as negative control, JQ1 (a pan-BET inhibitor) was used as positive control and all compounds were tested in constant percentage of DMSO (1%). After addition of 50 μL Cell Titer-GLO, shaking 2 minutes and incubating at room temperature 10 minutes, the Luminescence was measured using a Centro luminometer LB960 (Berthold). Dose-response curves were generated and effective dose 50 values ($EC_{50}$) were calculated using non-linear regression analysis (Graph Pad Prism).

TABLE 6

Effect of various compounds of invention on cell viability (Jurkat and Molm14 cells)[a]

| Compound | Cell line ($IC_{50}$ μM)[a] | |
|---|---|---|
| | Jurkat | Molm |
| 5b | 9.3 | ND |
| 24b | 14.2 | 10.2 |
| 25a | 13.5 | 9.9 |
| 25b | 5.2 | 11.1 |
| 25c | 6.1 | 14.8 |
| 27b | NA | NA |
| 27c | 39.5 | ND |
| 29b | 26.5 | 10.6 |
| 29c | 6.9 | 8.9 |
| 30c | 10.3 | 9.2 |
| 31a | 19.4 | 1.8 |
| 32a | 23.3 | 30.2 |
| 32c | 32.5 | ND |

TABLE 6-continued

Effect of various compounds of invention on cell viability (Jurkat and Molm14 cells)[a]

| Compound | Cell line ($IC_{50}$ μM)[a] | |
|---|---|---|
| | Jurkat | Molm |
| 42c | ND | 12.2 |
| 43c | 17.6 | 6.1 |
| 44b | ND | 23.7 |
| 44c | ND | 9.3 |

[a]Drug concentration that inhibits cell proliferation by 50%. Data are the mean of three experiments.
ND abbreviation stands for Not Determined.
NA abbreviation stands for Not Applicable ($IC_{50}$ > maximal concentration of compound used).

Example 6: Brds(BD1) Selective Inhibition

Figure 2:
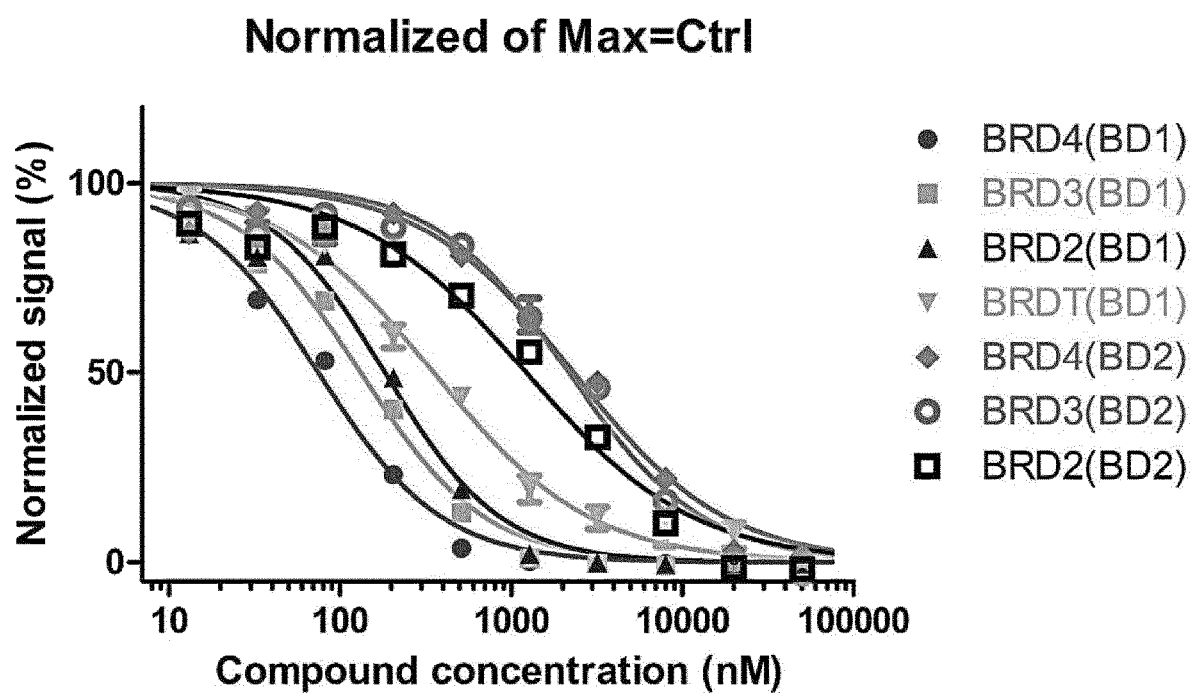
FIG. 2. Homogeneous Times Resolved Fluorescence (HTRF) selectivity assay of 43c on all BET members. Excitation at 337 nm, energy transfer at 620 nm, and fluorescence emission at 665 nm. Fluorescence data are normalized and plotted as a function of the ligand concentration.
Figure 3:
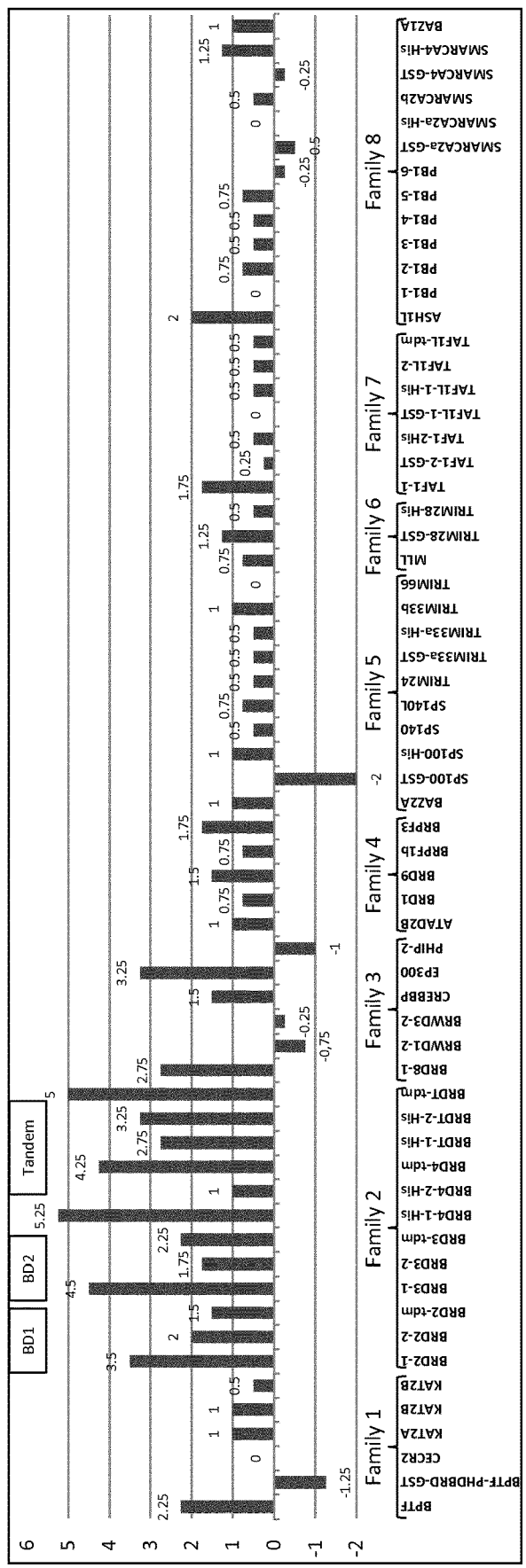
FIG. 3. Thermal Shift Assay (TSA) of 43c. The evaluation was performed on 61 bromodomains. A cut-off at +/−3.5° C. was set. 43c stabilizes only BRD4 (BD1) and BRD3 (BD1), with +4.5° C. and +5.25° C., respectively.

Molecule 43c was selected for more circumstantial evaluation. 43c demonstrates the best affinity to Brd4 (BD1) with $IC_{50}$ value of 74 nM, determined by HTRF. This activity was further validated by isothermal titration calorimetry (ITC), as orthogonal assay, displaying KD of 90 nM (FIG. 1). 43c displayed 7 to 31-folds preferential binding toward the first bromodomain vs the second one, according to HTRF evaluation (FIG. 2). Its selectivity profile was confirmed by BROMOscan assays, revealed $K_D$ value of 32 nM for Brd4 (BD1) as well as unforeseen selectivity ratio up to 313-fold to the first bromodomain. Selectivity of 43c was also studied against 61 bromodomains using a thermal melt stability assay (BromoMELT) (FIG. 3). 43c was found to stabilize only BET proteins with clear preference for Brd4 (BD1) (ΔTm=+5.25° C.) and Brd3 (BD1) (ΔTm=+4.5° C.).

Figure 4:
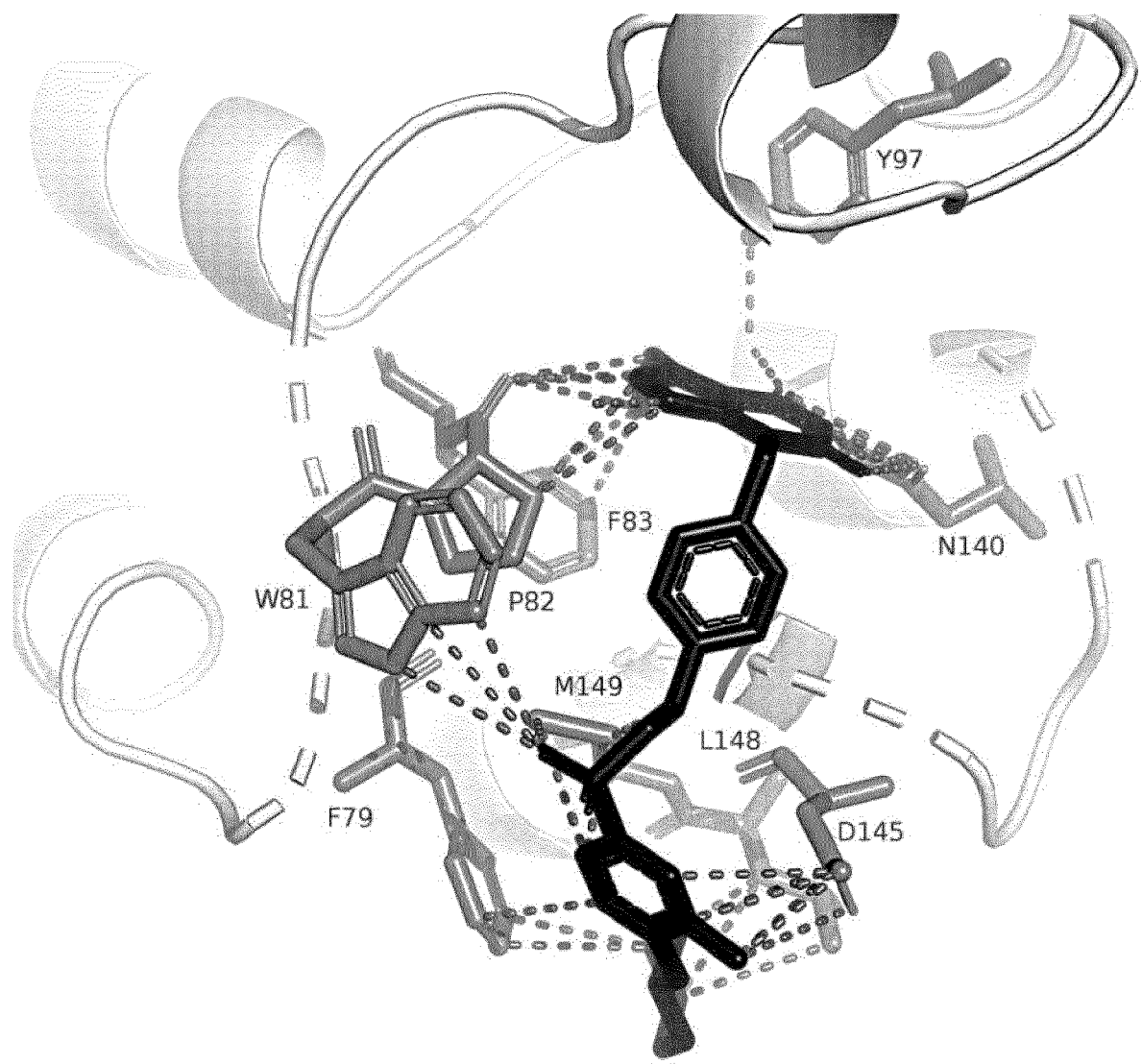
FIG. 4. Molecular mode of action of 43c in the N-acetylated binding pocket of Brd4 (BD1). Three dimensional crystallographic structure of 43c (black stick representation) in complex with Brd4 (BD1) showing some conserved residues (grey stick representation). Water molecules are presented as spheres. Hydrogen bond and van der Waals interactions of 43c are shown as grey dashed lines.

Crystallographic structures of compound 43c in complex with Brd4 (BD1) was resolved and compared to previously observed structures of 30c and 31a. As expected, the xanthine core of 43c forms canonical hydrogen bonds with N140 and Y97, found in all other complexes. Sulfonamide group establishes water mediated hydrogen bond with W81 as well as van der Waals interactions with amino acid residues of the WPF shelf (W81, P82 and F83). Comparison of van der Waals interactions provided by the phenyloxyoxane vs corresponding moieties of molecules 30c and 31a showed similar contacts with F79, D145, L148, and M149. The superimposition of structures revealed a perfect match of compounds at the xanthine-methylbenzylsulfonamide moiety as well as at the benzene-substituted fragment (FIG. 4).

Comparative analysis of protein/ligand interactions, including hydrophobic and hydrogen-bonding contacts, was carried out for selective inhibitors 30c, 31a and 43c (Table 7).

TABLE 7

Comparison of interactions in complexes 30c, 31a and 43c with Brd4(BD1)

| | interaction | residue | xanthine | benzenesulfonamide |
|---|---|---|---|---|
| 30c | Hydrogen | N140 | N140 | |
| 31a | bond | N140 | N140 | |
| 43c | | N140 | N140 | |
| 30c | Hydrogen | W81, Q85, Y97, D145 | Q85, Y97 | W81, D145 |
| 31a | bond | W81, Q85, Y97 | Q85, Y97 | W81 |
| 43c | mediated | W81, Q85, Y97 | Q85, Y97 | W81 |
| 30c | Van der Waals | F79, P82, F83, V87, L92, L94, D145, I146, | P82, F83, V87, L92, | F79, D145, L148, M149 |

TABLE 7-continued

Comparison of interactions in complexes 30c, 31a and 43c with Brd4(BD1)

| | interaction residue | | xanthine | benzenesulfonamide |
|---|---|---|---|---|
| | | L148, M149 | L94, I146 | |
| 31a | F79, P82, F83, V87, | | P82, F83, | F79, D145, |
| | L92, L94, D145, I146, | | V87, L92, | M149 |
| | M149 | | L94, I146 | |
| 43c | F79, W81, P82, F83, | | P82, F83, | F79, D145, L148, |
| | V87, L92, L94, D145, | | V87, L92, | M149 |
| | I146, L148, M149 | | L94, I146 | |

All three molecules displayed significant van der Waals interactions with side chains of phenylalanine F79, aspartic acid D145 and methionine M149 on both sides of the WPF groove. 30c and 31a also interact with leucine L148 at the BC loop. Interestingly, three of four residues, F79, D145, and L148, are unique for the first bromodomains and replaced by corresponding tyrosine, glutamic acid and alanine in the second bromodomain. Supposedly, van der Waals interactions of benzenesulfonamide moiety with these BD1-conserved residues allow the preferential inhibition of BET-BD1 domains. This finding suggests a potential mechanism for the selectivity of BET bromodomains.

For additional evaluation of the effect of 43c in cell assays, an influence of the molecule on c-Myc expression was determined by c-Myc HTRF. c-Myc is a proto-oncogene that is often overexpressed in cancer. This leads to the increased expression of many genes, involved in cell proliferation, contributing to cancer development. Downregulation of c-Myc is considered as a promising approach for anticancer treatment. Most of known to date potent pan-BET inhibitors, such as JQ1 or I-BET151, display strong downregulation of c-Myc, whereas BD2-selective inhibitor RVX-208 has no significant effect on the expression of this proto-oncogene. BD1-selective inhibitor 43c was found to downregulate c-Myc on Jurkat and CEM cell lines at 2.4 and 2.6 μM, respectively, those not only confirming cell efficiency of 43c, but also demonstrating a key role of the first bromodomain in c-Myc expression.

Thus, molecule 43c is, to date, the most potent and selective inhibitor of the BD1-domain, and has the necessary and sufficient criteria, including cellular activity, to further evaluation as a probe in more complex biological systems.

The invention claimed is:
1. A compound having the following formula (I):

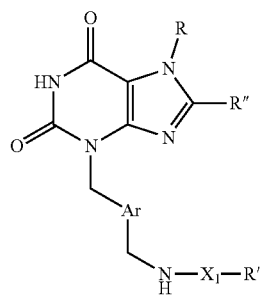

(I)

wherein:
R is a $(C_1-C_6)$alkyl group;
R" is H or a group having the following formula (A):

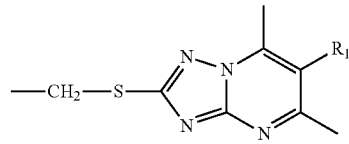

(A)

wherein $R_1$ is H or a $(C_1-C_6)$alkyl group;
Ar is a $(C_5-C_{12})$arylene radical;
$X_1$ is —C(=O)— or —SO$_2$—; and
R' is selected from the group consisting of:
$(C_1-C_6)$alkyl groups, optionally substituted with one or more substituents selected from the group consisting of:
$(C_5-C_{12})$aryl, optionally substituted by a $(C_1-C_6)$alkyl group,
—OR$_a$, R$_a$ being H or $(C_1-C_6)$alkyl,
—NH$_2$,
NH—C(=O)—O—$(C_1-C_6)$alkyl, and
(hetero)cycloalkyl;
heteroaryl groups,
optionally substituted with one or more substituents selected from the group consisting of:
$(C_1-C_6)$alkyl,
$(C_5-C_{12})$aryl, and
heteroaryl groups, optionally substituted by a $(C_1-C_6)$alkyl group;
$(C_5-C_{12})$aryl groups, optionally fused with one heterocycloalkyl or heteroaryl group, optionally substituted with one or more substituents selected from the group consisting of $(C_1-C_6)$alkyl, and COR$_2$, R$_2$ being a $(C_1-C_6)$alkyl group;
said aryl group being optionally substituted with one or more substituents selected from the group consisting of:
$(C_1-C_6)$alkyl,
$(C_5-C_{12})$aryl,
heteroaryl, optionally substituted by a $(C_1-C_6)$alkyl group,
halogen,
—CH$_2$-heteroaryl,
heterocycloalkyl, optionally fused with a phenyl group,
—NO$_2$,
—OR$_a$, R$_a$ being selected from the group consisting of:
H,
$(C_1-C_6)$alkyl,
$(C_5-C_{12})$aryl, optionally substituted with a substituent chosen from the halo$(C_1-C_6)$alkyl groups,
cycloalkyl,
heteroaryl, optionally substituted with a $(C_1-C_6)$alkyl group,
heterocycloalkyl, optionally substituted with a $(C_1-C_6)$alkyl group or a $(C_1-C_6)$alkylene-$(C_2-C_6)$alkynyl group, and
—CH$_2$—$(C_5-C_{12})$aryl,
—C(=O)—R$_e$, R$_e$ being a heterocycloalkyl,
—NR$_b$R$_c$, R$_b$ and R$_c$ being, independently of one another, H or $(C_1-C_6)$alkyl, and
—NHC(=O)R$_d$, R$_d$ being a $(C_1-C_6)$alkyl group; and
(hetero)cycloalkyl groups, comprising 5 or 6 atoms and optionally one heteroatom, optionally substituted with one or more substituents selected from the group consisting of:

($C_1$-$C_6$)alkyl,

—C(=O)$R_d$, $R_d$ being a ($C_1$-$C_6$)alkyl group,

—O$R_d$, $R_d$ being a ($C_1$-$C_6$)alkyl group,

—$CH_2$—O$R_d$, $R_d$ being a ($C_1$-$C_6$)alkyl group, ($C_5$-$C_{12}$)aryl,

—C(=O)O$R_a$, $R_d$ being a ($C_1$-$C_6$)alkyl group,

—$CH_2$—NHC(=O)O$R_a$, $R_d$ being a ($C_1$-$C_6$)alkyl group, and

—NHC(=O)O$R_a$, $R_d$ being a ($C_1$-$C_6$)alkyl group;

or a pharmaceutically acceptable salt and/or tautomeric form thereof, or its racemates, diastereomers or enantiomers.

2. The compound of claim 1, having the following formula (II):

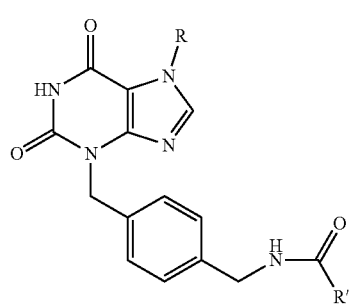

(II)

wherein R and R' are as defined in claim 1.

3. The compound of claim 1, having the following formula (III):

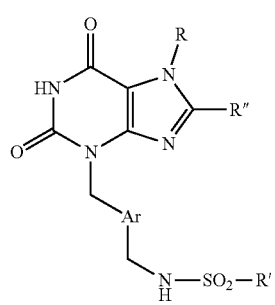

(III)

wherein:

Ar, R, and R" are as defined in claim 1;

R' is selected from the group consisting of:

($C_1$-$C_6$)alkyl groups, optionally substituted with one or more substituents selected from the group consisting of:

($C_5$-$C_{12}$)aryl, optionally substituted by a ($C_1$-$C_6$)alkyl group,

—O$R_a$, $R_a$ being H or ($C_1$-$C_6$)alkyl,

—$NH_2$,

NH—C(=O)—O—($C_1$-$C_6$)alkyl, and (hetero)cycloalkyl;

heteroaryl groups, optionally substituted with one or more substituents selected from the group consisting of:

($C_1$-$C_6$)alkyl, ($C_5$-$C_{12}$)aryl, and heteroaryl groups, optionally substituted by a ($C_1$-$C_6$)alkyl group; and ($C_5$-$C_{12}$)aryl groups, optionally fused with one heterocycloalkyl or heteroaryl group, optionally substituted with one or more substituents selected from the group consisting of: ($C_1$-$C_6$)alkyl or $COR_2$, $R_2$ being a ($C_1$-$C_6$)alkyl group;

said aryl group being optionally substituted with one or more substituents selected from the group consisting of:

($C_1$-$C_6$)alkyl, ($C_5$-$C_{12}$)aryl, heteroaryl, optionally substituted by a ($C_1$-$C_6$)alkyl group, halogen, —$CH_2$-heteroaryl, heterocycloalkyl, optionally fused with a phenyl group,

—$NO_2$,

—O$R_a$, $R_a$ being selected from the group consisting of:

H, ($C_1$-$C_6$)alkyl, ($C_5$-$C_{12}$)aryl, optionally substituted with a halo ($C_1$-$C_6$)alkyl group, cycloalkyl, heteroaryl, optionally substituted with a ($C_1$-$C_6$) alkyl group, heterocycloalkyl, optionally substituted with a ($C_1$-$C_6$)alkyl group or a ($C_1$-$C_6$)alkylene-($C_2$-$C_6$)alkynyl group, and —$CH_2$—($C_5$-$C_{12}$)aryl, —C(=O)—$R_e$, $R_e$ being a heterocycloalkyl, —$NR_bR_c$, $R_b$ and $R_c$ being, independently of one another, H or ($C_1$-$C_6$)alkyl, and —NHC(=O)$R_d$, $R_d$ being a ($C_1$-$C_6$)alkyl group.

4. The compound of claim 1, wherein Ar is a phenylene (—$C_6H_4$—) radical.

5. The compound of claim 1, wherein R" is H.

6. The compound of claim 1, wherein R is methyl or ethyl.

7. The compound of claim 1, having the following formula (IV):

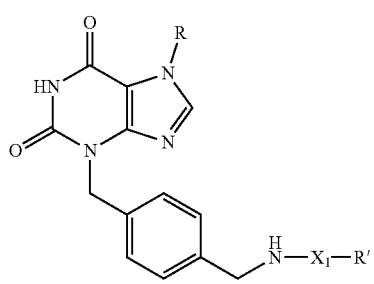

(IV)

wherein:

R is methyl or ethyl, and $X_1$ and R' are as defined in claim 1.

8. The compound having the following formula (V):

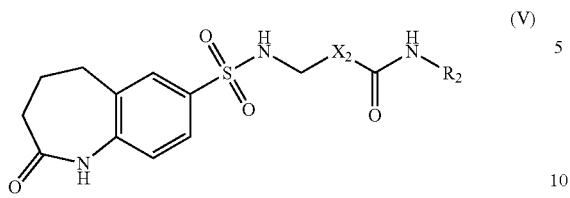

wherein:
X$_2$ is a cycloalkylene or phenylene group, and
R$_2$ is a (C$_1$-C$_6$)alkyl group, substituted by a heteroaryl group, said heteroaryl group being optionally substituted by a (C$_1$-C$_6$)alkyl group,
or a pharmaceutically acceptable salt and/or tautomeric form thereof, or its racemates, diastereomers or enantiomers.

9. The compound of claim 1, further comprising an excipient suitable for use as a medicament.

10. A pharmaceutical composition, comprising a compound according to claim 1, and at least one pharmaceutically acceptable excipient.

11. A method of treating a condition selected from the group consisting of cancer, inflammatory disease, sepsis, autoimmune disease, neurodegenerative disease, cardiovascular disorder, renal disorder, viral infection, and obesity comprising administering to a patient in need thereof a pharmaceutically acceptable amount of the compound of claim 1.

* * * * *